United States Patent
Wen et al.

(10) Patent No.: US 11,819,516 B2
(45) Date of Patent: Nov. 21, 2023

(54) IMMUNOTHERAPY

(71) Applicant: THE REGENTS OF THE UNIVERSITY OF MICHIGAN, Ann Arbor, MI (US)

(72) Inventors: Fei Wen, Ann Arbor, MI (US); Mason Smith, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 317 days.

(21) Appl. No.: 15/773,952

(22) PCT Filed: Nov. 4, 2016

(86) PCT No.: PCT/US2016/060513
§ 371 (c)(1),
(2) Date: May 4, 2018

(87) PCT Pub. No.: WO2017/079545
PCT Pub. Date: May 11, 2017

(65) Prior Publication Data
US 2018/0318351 A1  Nov. 8, 2018

Related U.S. Application Data

(60) Provisional application No. 62/252,043, filed on Nov. 6, 2015.

(51) Int. Cl.
| | |
|---|---|
| *C12N 15/62* | (2006.01) |
| *C12N 5/0783* | (2010.01) |
| *C07K 14/39* | (2006.01) |
| *A61K 35/17* | (2015.01) |
| *A61K 48/00* | (2006.01) |
| *A61K 47/61* | (2017.01) |
| *A61K 47/68* | (2017.01) |
| *A61K 38/17* | (2006.01) |
| *C07K 19/00* | (2006.01) |

(52) U.S. Cl.
CPC .......... *A61K 35/17* (2013.01); *A61K 38/1774* (2013.01); *A61K 47/61* (2017.08); *A61K 47/6889* (2017.08); *A61K 48/00* (2013.01); *C07K 14/39* (2013.01); *C07K 19/00* (2013.01); *C12N 5/0636* (2013.01); *C12N 15/62* (2013.01); *C07K 2318/10* (2013.01); *C07K 2319/02* (2013.01); *C07K 2319/035* (2013.01)

(58) Field of Classification Search
None
See application file for complete search history.

(56) References Cited

FOREIGN PATENT DOCUMENTS

| | | |
|---|---|---|
| WO | WO 2001/94944 | 12/2001 |
| WO | WO 2015/051247 | 4/2015 |
| WO | WO 2017/079545 | 5/2017 |

OTHER PUBLICATIONS

Fairhead et al (JACS, 2014, 136: 12355-12363) (Year: 2014).*
Ali-Khan et al (Curr. Prot. Prot. Sci. 2002, 22.1.1-22.1.19, Suppl. 30, John Wiley & Sons, Inc.) (Year: 2002).*
Repana et al (Genome Biol. 2019 20: 1-12) (Year: 2019).*
Schumacher and Schreiber (Science, 2015, 348: 69-74) (Year: 2015).*
HLA Nomenclature (2015) (Year: 2015).*
Lloyd et al (Protein Engineering, Eng. Design & Selection, 2009, 22(3): 159-168) (Year: 2009).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Smith et al (ACS Synth. Biol. May 7, 2018, 7: 1629-1639) (Year: 2018).*
Lebedeva et al (Abstract of Curr. Opin. Immunol. 2005, 17(3): 251-258) (Year: 2005).*
Liu et al (MHC Complex: Interaction with Peptides. IN: eLS. John Wiley & Songs, Ltd: Chinchester, DOI: 10.1002/9780470015902. a0000922.pub2, 2011, pp. 1-12) (Year: 2011).*
Wieczorek et al (Front. Immunol. 2017, vol. 8, article 292: 1-16) (Year: 2017).*
Pullen et al (J. Immunol. 1994, 152: 3445-3451) (Year: 1994).*
Marrack et al (Ann. Rev. Immunol. 2008, 26:171-203) (Year: 2008).*
Singh et al (J. Immunol. 2017, 199: 2203-2213) (Year: 2017).*
Adams et al., HLA class I and II genotype of the NCI-60 cell lines. J Transl Med. Mar. 4, 2005;3(1):11.
Alarcon et al., The immunological synapse: a cause or consequence of T-cell receptor triggering? Immunology. Aug. 2011;133(4):420-5.
Al-Hajj et al., Prospective identification of tumorigenic breast cancer cells. Proc Natl Acad Sci U S A. Apr. 1, 2003;100(7):3983-8.
Altman et al., Phenotypic analysis of antigen-specific T lymphocytes. Science. Oct. 4, 1996;274(5284):94-6.
Bakker et al., Conditional MHC class I ligands and peptide exchange technology for the human MHC gene products HLA-A1, -A3, -A11, and -B7. Proc Natl Acad Sci U S A. Mar. 11, 2008;105(10):3825-30.
Bayer et al., From cellulosomes to cellulosomics. Chem Rec. 2008;8(6):364-77.
Bayer et al., The cellulosomes: multienzyme machines for degradation of plant cell wall polysaccharides. Annu Rev Microbiol. 2004;58:521-54.

(Continued)

*Primary Examiner* — G. R. Ewoldt
*Assistant Examiner* — Marianne DiBrino
(74) *Attorney, Agent, or Firm* — CASIMIR JONES S.C.; Thomas A. Isenbarger

(57) ABSTRACT

Provided herein is technology relating to immunotherapy and particularly, but not exclusively, to compositions, methods, and kits for immunotherapy and activation of T cells using a peptide-major histocompatibility complex (pMHC) assembled on a protein scaffold for patterned signal presentation of T cell activating ligands to T cells.

15 Claims, 13 Drawing Sheets

Specification includes a Sequence Listing.

(56) References Cited

OTHER PUBLICATIONS

Becker et al., Immune-suppressive properties of the tumor microenvironment. Cancer Immunol Immunother. Jul. 2013;62(7):1137-48.
Berger et al., Adoptive transfer of effector CD8+ T cells derived from central memory cells establishes persistent T cell memory in primates. J Clin Invest. Jan. 2008;118(1):294-305.
Boder et al., Yeast surface display for screening combinatorial polypeptide libraries. Nat Biotechnol. Jun. 1997;15(6):553-7.
Brodie et al., In vivo migration and function of transferred HIV-1-specific cytotoxic T cells. Nat Med. Jan. 1999;5(1):34-41.
Bromley et al., The immunological synapse. Annu Rev Immunol. 2001;19:375-96.
Brossard et al., Multifocal structure of the T cell—dendritic cell synapse. Eur J Immunol. Jun. 2005;35(6):1741-53.
Butterfield. Dendritic cells in cancer immunotherapy clinical trials: are we making progress? Front Immunol. Dec. 13, 2013;4:454.
Call et al., In vivo enhancement of peptide display by MHC class II molecules with small molecule catalysts of peptide exchange. J Immunol. May 15, 2009;182(10):6342-52.
CDD Accession No. cd00174 (2020) 6 pages.
CDD Accession No. cd08546 (2013) 2 pages.
CDD Accession No. cd14253 (2014) 2 pages.
Chapuis et al., Transferred melanoma-specific CD8+ T cells persist, mediate tumor regression, and acquire central memory phenotype. Proc Natl Acad Sci U S A. Mar. 20, 2012;109(12):4592-7.
Chattopadhyay et al., Structural basis of inducible costimulator ligand costimulatory function: determination of the cell surface oligomeric state and functional mapping of the receptor binding site of the protein. J Immunol. Sep. 15, 2006;177(6):3920-9.
Chen et al., Chemoimmunotherapy: reengineering tumor immunity. Cancer Immunol Immunother. Feb. 2013;62(2):203-16.
Chen et al., Directed evolution of homing endonuclease I-SceI with altered sequence specificity. Protein Eng Des Sel. Apr. 2009;22(4):249-56.
Cho et al., Elastic-net regularization approaches for genome-wide association studies of rheumatoid arthritis. BMC Proc. Dec. 15, 2009;3 Suppl 7(Suppl 7):S25. 6 pages.
Cowburn. Peptide recognition by PTB and PDZ domains. Curr Opin Struct Biol. Dec. 1997;7(6):835-8.
Cox. Recombinant protein vaccines produced in insect cells. Vaccine. Feb. 27, 2012;30(10):1759-66.
Cull et al., Biotinylation of proteins in vivo and in vitro using small peptide tags. Methods Enzymol. 2000;326:430-40.
Curado et al., "Cell biology meets physiology: functional organization of vertebrate plasma membranes"—the immunological synapse. Curr Top Membr. 2013;72:313-46.
Darcy et al., Manipulating immune cells for adoptive immunotherapy of cancer. Curr Opin Immunol. Apr. 2014;27:46-52.
Davila et al., Efficacy and toxicity management of 19-28z CAR T cell therapy in B cell acute lymphoblastic leukemia. Sci Transl Med. Feb. 19, 2014;6(224):224ra25. 23 pages.
Davis et al., What is the importance of the immunological synapse? Trends Immunol. Jun. 2004;25(6):323-7.
Day et al., Ex vivo analysis of human memory CD4 T cells specific for hepatitis C virus using MHC class II tetramers. J Clin Invest. Sep. 2003;112(6):831-42.
Demain et al., Production of recombinant proteins by microbes and higher organisms. Biotechnol Adv. May-Jun. 2009;27(3):297-306.
Demond et al., Interrogating the T cell synapse with patterned surfaces and photoactivated proteins. Curr Opin Immunol. Dec. 2007;19(6):722-7.
Ding et al., Cellulosomal scaffoldin-like proteins from Ruminococcus flavefaciens. J Bacteriol. Mar. 2001;183(6):1945-53.
Doh et al., Immunological synapse arrays: patterned protein surfaces that modulate immunological synapse structure formation in T cells. Proc Natl Acad Sci U S A. Apr. 11, 2006;103(15):5700-5.
Dong et al., Metabolic influences that regulate dendritic cell function in tumors. Front Immunol. Jan. 30, 2014;5:24. 7 pages.
Doubrovina et al., Adoptive immunotherapy with unselected or EBV-specific T cells for biopsy-proven EBV+ lymphomas after allogeneic hematopoietic cell transplantation. Blood. Mar. 15, 2012;119(11):2644-56.
DSM 1313. Acetivibrio thermocellus. Accession No. NC_017304. 2021. 2 pages.
Dudley et al., Adoptive cell therapy for patients with metastatic melanoma: evaluation of intensive myeloablative chemoradiation preparative regimens. J Clin Oncol. Nov. 10, 2008;26(32):5233-9.
Dudley et al., Cancer regression and autoimmunity in patients after clonal repopulation with antitumor lymphocytes. Science. Oct. 25, 2002;298(5594):850-4.
Dueber et al., Synthetic protein scaffolds provide modular control over metabolic flux. Nat Biotechnol. Aug. 2009;27(8):753-9.
Durai et al., In vivo functional efficacy of tumor-specific T cells expanded using HLA-Ig based artificial antigen presenting cells (aAPC). Cancer Immunol Immunother. Feb. 2009;58(2):209-20.
Dustin et al., A novel adaptor protein orchestrates receptor patterning and cytoskeletal polarity in T-cell contacts. Cell. Sep. 4, 1998;94(5):667-77.
Dustin et al., New insights into the T cell synapse from single molecule techniques. Nat Rev Immunol. Sep. 9, 2011;11(10):672-84.
Feinberg et al., Complete genome sequence of the cellulolytic thermophile Clostridium thermocellum DSM1313. J Bacteriol. Jun. 2011;193(11):2906-7.
Fontes et al., Cellulosomes: highly efficient nanomachines designed to deconstruct plant cell wall complex carbohydrates. Annu Rev Biochem. 2010;79:655-81.
Freeman et al., Murine B7-2, an alternative CTLA4 counter-receptor that costimulates T cell proliferation and interleukin 2 production. J Exp Med. Dec. 1, 1993;178(6):2185-92.
Friedl et al., Tuning immune responses: diversity and adaptation of the immunological synapse. Nat Rev Immunol. Jul. 2005;5(7):532-45.
Gajewski et al., Innate and adaptive immune cells in the tumor microenvironment. Nat Immunol. Oct. 2013;14(10):1014-22.
Gardner et al., Sipuleucel-T (Provenge) autologous vaccine approved for treatment of men with asymptomatic or minimally symptomatic castrate-resistant metastatic prostate cancer. Hum Vaccin Immunother. Apr. 2012;8(4):534-9.
GenBank Accession No. AF155197 (1999) 3 pages.
GenBank Accession No. AF224509 (2004) 8 pages.
GenBank Accession No. AY221112 (2003) 2 pages.
GenBank Accession No. AY221113 (2003) 2 pages.
GenBank Accession No. Q06851 (2020) 8 pages.
GenBank Accession No. Q06852 (2020) 4 pages.
GenBank Accession No. Q06853 (2020) 3 pages.
GenBank Accession No. U40345 (2020) 4 pages.
GenBank Accession No. U49980 (1996) 2 pages.
GenBank Accession No. WP_015924274 (2013) 1 page.
GenBank Accession No. WP_015924614 (2020) 2 pages.
GenBank Accession No. WP_020458017 (2015) 3 pages.
GenBank Accession No. WP_020458018 (2020) 3 pages.
GenBank Accession No. YP_001039466 (2014) 5 pages.
Gerngross et al., Sequencing of a Clostridium thermocellum gene (cipA) encoding the cellulosomal SL-protein reveals an unusual degree of internal homology. Mol Microbiol. Apr. 1993;8(2):325-34.
Gerngross. Advances in the production of human therapeutic proteins in yeasts and filamentous fungi. Nat Biotechnol. Nov. 2004;22(11):1409-14.
Gnjatic et al., Accumulation of the p53 protein allows recognition by human CTL of a wild-type p53 epitope presented by breast carcinomas and melanomas. J Immunol. Jan. 1, 1998;160(1):328-33.
Goff et al., Tumor infiltrating lymphocyte therapy for metastatic melanoma: analysis of tumors resected for TIL. J Immunother. Oct. 2010;33(8):840-7.
Grakoui et al., The immunological synapse: a molecular machine controlling T cell activation. Science. Jul. 9, 1999;285(5425):221-7.
Grewal et al., The role of CD40 ligand in costimulation and T-cell activation. Immunol Rev. Oct. 1996;153:85-106.

(56) References Cited

OTHER PUBLICATIONS

Guo et al., Therapeutic cancer vaccines: past, present, and future. Adv Cancer Res. 2013;119:421-75.

Harty et al., Shaping and reshaping CD8+ T-cell memory. Nat Rev Immunol. Feb. 2008;8(2):107-19.

Haynes et al., Single-chain antigen recognition receptors that costimulate potent rejection of established experimental tumors. Blood. Nov. 1, 2002;100(9):3155-63.

Helmy et al., Cancer immunotherapy: accomplishments to date and future promise. Ther Deliv. Oct. 2013;4(10):1307-20.

Huber et al., Interdisciplinary critique of sipuleucel-T as immunotherapy in castration-resistant prostate cancer. J Natl Cancer Inst. Feb. 22, 2012;104(4):273-9.

Huppa et al., T-cell-antigen recognition and the immunological synapse. Nat Rev Immunol. Dec. 2003;3(12):973-83.

Immune Epitope Database. Epitope No. 119507. Retrieved from internet Aug. 17, 2020. 1 page.

Immune Epitope Database. Epitope No. 13572. Retrieved from internet Aug. 17, 2020. 1 page.

Immune Epitope Database. Epitope No. 48237. Retrieved from internet Aug. 17, 2020. 1 page.

Immune Epitope Database. Epitope No. 97487. Retrieved from internet Aug. 17, 2020. 1 page.

Inter Pro. Accession No. IPR001452. Retrieved from internet Aug. 17, 2020. 11 pages.

InterPro Accession No. IPR002102. Retrieved from internet Aug. 17, 2020. 1 page.

InterPro Accession No. IPR002105. Retrieved from internet Aug. 17, 2020. 1 page.

Irvine et al., Direct observation of ligand recognition by T cells. Nature. Oct. 24, 2002;419(6909):845-9.

Irvine et al., Patterned surfaces as tools to study ligand recognition and synapse formation by T cells. Curr Opin Immunol. Aug. 2007;19(4):463-9.

Jiang et al., HLA Tetramer Based Artificial Antigen-Presenting Cells Efficiently Stimulate CTLs Specific for Malignant Glioma. Clin Cancer Res. Dec. 15, 2007;13(24):7329-34.

Jindou et al., Cohesin-dockerin interactions within and between Clostridium josui and Clostridium thermocellum: binding selectivity between cognate dockerin and cohesin domains and species specificity. J Biol Chem. Mar. 12, 2004;279(11):9867-74.

Kakiuchi et al., Cloning and DNA sequencing of the genes encoding Clostridium josui scaffolding protein CipA and cellulase CelD and identification of their gene products as major components of the cellulosome. J Bacteriol. Aug. 1998;180(16):4303-8.

Kalos et al., Adoptive T cell transfer for cancer immunotherapy in the era of synthetic biology. Immunity. Jul. 25, 2013;39(1):49-60.

Kantoff et al., Sipuleucel-T immunotherapy for castration-resistant prostate cancer. N Engl J Med. Jul. 29, 2010;363(5):411-22.

Kawakami et al., Cloning of the gene coding for a shared human melanoma antigen recognized by autologous T cells infiltrating into tumor. Proc Natl Acad Sci U S A. Apr. 26, 1994;91(9):3515-9.

Kim et al., The ABCs of artificial antigen presentation. Nat Biotechnol. Apr. 2004;22(4):403-10.

Kochenderfer et al., Eradication of B-lineage cells and regression of lymphoma in a patient treated with autologous T cells genetically engineered to recognize CD19. Blood. Nov. 18, 2010;116(20):4099-102.

Krummel et al., Dynamics of the immunological synapse: finding, establishing and solidifying a connection. Curr Opin Immunol. Feb. 2002;14(1):66-74.

Le et al., Next-generation cancer vaccine approaches: integrating lessons learned from current successes with promising biotechnologic advances. J Natl Compr Canc Netw. Jul. 2013;11(7):766-72.

Leen et al., Monoculture-derived T lymphocytes specific for multiple viruses expand and produce clinically relevant effects in immunocompromised individuals. Nat Med. Oct. 2006;12(10):1160-6.

Liu et al., Functional assembly of a multi-enzyme methanol oxidation cascade on a surface-displayed trifunctional scaffold for enhanced NADH production. Chem Commun (Camb). May 8, 2013;49(36):3766-8.

Lutzky et al., Cytotoxic T cell adoptive immunotherapy as a treatment for nasopharyngeal carcinoma. Clin Vaccine Immunol. Feb. 2014;21(2):256-9.

Lytle et al., Interactions of the CelS binding ligand with various receptor domains of the Clostridium thermocellum cellulosomal scaffolding protein, CipA. J Bacteriol. Feb. 1996;178(4):1200-3.

Maj et al., T cells and costimulation in cancer. Cancer J. Nov.-Dec. 2013;19(6):473-82.

Malek et al., CD4 regulatory T cells prevent lethal autoimmunity in IL-2Rbeta-deficient mice. Implications for the nonredundant function of IL-2. Immunity. Aug. 2002;17(2):167-78.

MBP epitope No. 13572. (2020) 1 page.

Mendel et al., Activated T cells express the OX40 ligand: requirements for induction and costimulatory function. Immunology. Feb. 2006;117(2):196-204.

Middleton et al., New allele frequency database: http://www.allelefrequencies.net . Tissue Antigens. May 2003;61(5):403-7.

Mitchell et al., Phase I trial of adoptive immunotherapy with cytolytic T lymphocytes immunized against a tyrosinase epitope. J Clin Oncol. Feb. 15, 2002;20(4):1075-86.

Monks et al., Three-dimensional segregation of supramolecular activation clusters in T cells. Nature. Sep. 3, 1998;395(6697):82-6.

Morais et al., Cellulase-xylanase synergy in designer cellulosomes for enhanced degradation of a complex cellulosic substrate. mBio. Dec. 14, 2010;1(5):e00285-10. 8 pages.

Mossman et al., Altered TCR signaling from geometrically repatterned immunological synapses. Science. Nov. 18, 2005;310(5751):1191-3.

Muller et al., Transfection of dendritic cells with RNA induces CD4-and CD8-mediated T cell immunity against breast carcinomas and reveals the immunodominance of presented T cell epitopes. J Immunol. Jun. 15, 2003;170(12):5892-6.

Nepom et al., HLA class II tetramers: tools for direct analysis of antigen-specific CD4+ T cells. Arthritis Rheum. Jan. 2002;46(1):5-12.

Newell et al., Cytometry by time-of-flight shows combinatorial cytokine expression and virus-specific cell niches within a continuum of CD8+ T cell phenotypes. Immunity. Jan. 27, 2012;36(1):142-52.

Newell et al., Simultaneous detection of many T-cell specificities using combinatorial tetramer staining. Nat Methods. Jul. 2009;6(7):497-9.

Novellino et al., A listing of human tumor antigens recognized by T cells: Mar. 2004 update. Cancer Immunol Immunother. Mar. 2005;54(3):187-207.

NP epitope No. 97487. Retrieved from internet Aug. 17, 2020. 1 page.

Numbenjapon et al., Antigen-independent and antigen-dependent methods to numerically expand CD19-specific CD8+ T cells. Exp Hematol. Jul. 2007;35(7):1083-90.

Pages et al., Sequence analysis of scaffolding protein CipC and ORFXp, a new cohesin-containing protein in Clostridium cellulolyticum: comparison of various cohesin domains and subcellular localization of ORFXp. J Bacteriol. Mar. 1999;181(6):1801-10.

Pawson et al., SH2 and SH3 domains. Curr Biol. Jul. 1, 1993;3(7):434-42.

Peach et al., Both extracellular immunoglobin-like domains of CD80 contain residues critical for binding T cell surface receptors CTLA-4 and CD28. J Biol Chem. Sep. 8, 1995;270(36):21181-7.

Piao et al., Enhancement of T-cell-mediated anti-tumour immunity via the ectopically expressed glucocorticoid-induced tumour necrosis factor receptor-related receptor ligand (GITRL) on tumours. Immunology. Aug. 2009;127(4):489-99.

Porter et al., A phase 1 trial of donor lymphocyte infusions expanded and activated ex vivo via CD3/CD28 costimulation. Blood. Feb. 15, 2006;107(4):1325-31.

Prosite Accession No. PS50002. Retrieved from internet Aug. 17, 2020. 3 pages.

(56) References Cited

OTHER PUBLICATIONS

Radford et al., Dendritic cells and cancer immunotherapy. Curr Opin Immunol. Apr. 2014;27:26-32.
Rapoport et al., Rapid immune recovery and graft-versus-host disease-like engraftment syndrome following adoptive transfer of Costimulated autologous T cells. Clin Cancer Res. Jul. 1, 2009;15(13):4499-507.
Remingtons Pharmaceutical Sciences, Mack Publishing Co. A. R. Gennaro ed. 1985. TOC only 4 pages.
Ribas et al., Determinant spreading and tumor responses after peptide-based cancer immunotherapy. Trends Immunol. Feb. 2003;24(2):58-61.
Richards et al., Infection of HLA-DR1 transgenic mice with a human isolate of influenza a virus (H1N1) primes a diverse CD4 T-cell repertoire that includes CD4 T cells with heterosubtypic cross-reactivity to avian (H5N1) influenza virus. J Virol. Jul. 2009;83(13):6566-77.
Robbins et al., Tumor regression in patients with metastatic synovial cell sarcoma and melanoma using genetically engineered lymphocytes reactive with NY-ESO-1. J Clin Oncol. Mar. 1, 2011;29(7):917-24.
Robinson et al., The IMGT/HLA database. Nucleic Acids Res. Jan. 2013;41(Database issue):D1222-7.
Rosenberg et al., Use of tumor-infiltrating lymphocytes and interleukin-2 in the immunotherapy of patients with metastatic melanoma. A preliminary report. N Engl J Med. Dec. 22, 1988;319(25):1676-80.
Saksela et al., SH3 domain ligand binding: What's the consensus and where's the specificity? FEBS Lett. Aug. 14, 2012;586(17):2609-14.
Schilbach et al., Cytotoxic minor histocompatibility antigen HA-1-specific CD8+ effector memory T cells: artificial APCs pave the way for clinical application by potent primary in vitro induction. Blood. Jul. 1, 2005;106(1):144-9.
Schweizer et al., Immunotherapy for prostate cancer: recent developments and future challenges. Cancer Metastasis Rev. Sep. 2014;33(2-3):641-55.
Seavey et al., Antiangiogenesis immunotherapy induces epitope spreading to Her-2/neu resulting in breast tumor immunoediting. Breast Cancer (Dove Med Press). Oct. 5, 2009;1:19-30.
Shevach et al., The GITR-GITRL interaction: co-stimulation or contrasuppression of regulatory activity? Nat Rev Immunol. Aug. 2006;6(8):613-8.
Shoseyov et al., Primary sequence analysis of Clostridium cellulovorans cellulose binding protein A. Proc Natl Acad Sci U S A. Apr. 15, 1992;89(8):3483-7.
Smart Accession No. SM00326. Retrieved from internet Aug. 17, 2020. 4 pages.
Stamper et al., Crystal structure of the B7-1/CTLA-4 complex that inhibits human immune responses. Nature. Mar. 29, 2001;410(6828):608-11.
Staunton et al., The arrangement of the immunoglobulin-like domains of ICAM-1 and the binding sites for LFA-1 and rhinovirus. Cell. Apr. 20, 1990;61(2):243-54.
Su et al., Virus-specific CD4(+) memory-phenotype T cells are abundant in unexposed adults. Immunity. Feb. 21, 2013;38(2):373-83.
Suhoski et al., Engineering artificial antigen-presenting cells to express a diverse array of co-stimulatory molecules. Mol Ther. May 2007;15(5):981-8.
Sun et al., Cloning and characterization of a panel of constitutive promoters for applications in pathway engineering in *Saccharomyces cerevisiae*. Biotechnol Bioeng. Aug. 2012;109(8):2082-92.
Sun et al., Direct conversion of xylan to ethanol by recombinant *Saccharomyces cerevisiae* strains displaying an engineered minihemicellulosome. Appl Environ Microbiol. Jun. 2012;78(11):3837-45.
Sunshine et al., Nanoengineering approaches to the design of artificial antigen-presenting cells. Nanomedicine (Lond). Jul. 2013;8(7):1173-89.

Thauland et al., Diversity in immunological synapse structure. Immunology. Dec. 2010;131(4):466-72.
Thomas et al., CD86 has sustained costimulatory effects on CD8 T cells. J Immunol. Nov. 1, 2007;179(9):5936-46.
Toebes et al., Design and use of conditional MHC class I ligands. Nat Med. Feb. 2006;12(2):246-51.
Tonikian et al., A specificity map for the PDZ domain family. PLoS Biol. Sep. 30, 2008;6(9):e239. 17 pages.
Turtle et al., Artificial antigen-presenting cells for use in adoptive immunotherapy. Cancer J. Jul.-Aug. 2010;16(4):374-81.
UniProtKB No. A9JJF6. Retrieved from internet Aug. 17, 2020. 6 pages.
UniProtKB No. P01101. Retrieved from internet Aug. 17, 2020. 10 pages.
UniProtKB No. P01903. Retrieved from internet Aug. 17, 2020. 17 pages.
UniProtKB No. P04233. Retrieved from internet Aug. 17, 2020. 12 pages.
UniProtKB No. P05627. Retrieved from internet Aug. 17, 2020. 13 pages.
UniProtKB No. P0C2S5. Retrieved from internet Aug. 17, 2020. 8 pages.
Van Der Bruggen et al., A gene encoding an antigen recognized by cytolytic T lymphocytes on a human melanoma. Science. Dec. 13, 1991;254(5038):1643-7.
Vicente et al., Large-scale production and purification of VLP-based vaccines. J Invertebr Pathol. Jul. 2011;107 Suppl:S42-8.
Vollers et al., Class II major histocompatibility complex tetramer staining: progress, problems, and prospects. Immunology. Mar. 2008;123(3):305-13.
Walter et al., Reconstitution of cellular immunity against cytomegalovirus in recipients of allogeneic bone marrow by transfer of T-cell clones from the donor. N Engl J Med. Oct. 19, 1995;333(16):1038-44.
Welten et al., The distinct role of T cell costimulation in antiviral immunity. Curr Opin Virol. Aug. 2013;3(4):475-82.
Wen et al., Cell surface display of functional human MHC class II proteins: yeast display versus insect cell display. Protein Eng Des Sel. Sep. 2011;24(9):701-9.
Wen et al., Construction and screening of an antigen-derived peptide library displayed on yeast cell surface for CD4+ T cell epitope identification. Methods Mol Biol. 2013;1061:245-64.
Wen et al., Protein engineering in designing tailored enzymes and microorganisms for biofuels production. Curr Opin Biotechnol. Aug. 2009;20(4):412-9.
Wen et al., Rapid identification of CD4+ T-cell epitopes using yeast displaying pathogen-derived peptide library. J Immunol Methods. Jul. 20, 2008;336(1):37-44.
Wen et al., Yeast surface display of trifunctional minicellulosomes for simultaneous saccharification and fermentation of cellulose to ethanol. Appl Environ Microbiol. Feb. 2010;76(4):1251-60.
Xie et al., How the immune system talks to itself: the varied role of synapses. Immunol Rev. Jan. 2013;251(1):65-79.
Yang et al., Structural basis for dimerization of ICAM-1 on the cell surface. Mol Cell. Apr. 2004;23;14(2):269-76.
Yee et al., Adoptive T cell therapy using antigen-specific CD8+ T cell clones for the treatment of patients with metastatic melanoma: in vivo persistence, migration, and antitumor effect of transferred T cells. Proc Natl Acad Sci U S A. Dec. 10, 2002;99(25):16168-73.
Yee et al., The use of endogenous T cells for adoptive transfer. Immunol Rev. Jan. 2014;257(1):250-63.
Zakrzewski et al., Adoptive transfer of T-cell precursors enhances T-cell reconstitution after allogeneic hematopoietic stem cell transplantation. Nat Med. Sep. 2006;12(9):1039-47.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
Zhang et al., 4-1BB is superior to CD28 costimulation for generating CD8+ cytotoxic lymphocytes for adoptive immunotherapy. J Immunol. Oct. 1, 2007;179(7):4910-8.
Zverlov et al., Mutations in the scaffoldin gene, cipA, of Clostridium thermocellum with impaired cellulosome formation and cellulose

(56) References Cited

OTHER PUBLICATIONS hydrolysis: insertions of a new transposable element, IS1447, and implications for cellulase synergism on crystalline cellulose. J Bacteriol. Jun. 2008;190(12):4321-7.
International Search Report and Written Opinion for PCT/US2016/060513. dated Feb. 16, 2017. 11 pages.

* cited by examiner

SEQUENCE LISTING

<160> NUMBER OF SEQ ID NOS: 37

<210> SEQ ID NO 1
<211> LENGTH: 14
<212> TYPE: PRT
<213> ORGANISM: simian parainfluenza virus 5

<400> SEQUENCE: 1

Gly Lys Pro Ile Pro Asn Pro Leu Leu Gly Leu Asp Ser Thr
1               5                   10

<210> SEQ ID NO 2
<211> LENGTH: 10
<212> TYPE: PRT
<213> ORGANISM: Homo sapiens

```
<400> SEQUENCE: 2

Glu Gln Lys Leu Ile Ser Glu Glu Asp Leu
1               5                   10

<210> SEQ ID NO 3
<211> LENGTH: 9
<212> TYPE: PRT
<213> ORGANISM: Homo sapiens

<400> SEQUENCE: 3

Tyr Pro Tyr Asp Val Pro Asp Tyr Ala
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa=Leucine or Isoleucine

<400> SEQUENCE: 4

Gly Ile Leu Gly Phe Val Phe Xaa Leu
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa=Leucine or Isoleucine

<400> SEQUENCE: 5

Ala Ala Arg Gly Xaa Thr Leu Ala Met
1               5

<210> SEQ ID NO 6
<211> LENGTH: 6
<212> TYPE: PRT
<213> ORGANISM: Homo sapiens

<400> SEQUENCE: 6

Leu Val Pro Arg Gly Ser
1               5

<210> SEQ ID NO 7
<211> LENGTH: 8
<212> TYPE: PRT
<213> ORGANISM: Rhinovirus

<400> SEQUENCE: 7

Leu Glu Val Leu Phe Gln Gly Pro
1               5

<210> SEQ ID NO 8
<211> LENGTH: 15
<212> TYPE: PRT
<213> ORGANISM: Artificial sequence
<220> FEATURE:
```

```
<223> OTHER INFORMATION: Synthetic peptide

<400> SEQUENCE: 8

Gly Leu Asn Asp Ile Phe Glu Ala Gln Lys Ile Glu Trp His Glu
1               5                   10                  15

<210> SEQ ID NO 9
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 9

Pro Xaa Xaa Pro
1

<210> SEQ ID NO 10
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa= Any Aliphatic amino acid
<220> FEATURE:
<221> NAME/KEY: MISC_FEATURE
<222> LOCATION: (3)..(3)
<223> OTHER INFORMATION: Xaa= Sometimes Proline
<220> FEATURE:
<221> NAME/KEY: MISC_FEATURE
<222> LOCATION: (4)..(4)
<223> OTHER INFORMATION: Xaa= Any Aliphatic amino acid

<400> SEQUENCE: 10

Xaa Pro Xaa Xaa Pro
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 11

Arg Xaa Xaa Lys
1

<210> SEQ ID NO 12
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
```

```
<222> LOCATION: (6)..(7)
<223> OTHER INFORMATION: Xaa can be any naturally occurring amino acid

<400> SEQUENCE: 12

Arg Lys Xaa Xaa Pro Xaa Xaa Pro
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Pro Xaa Xaa Pro Xaa Arg
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Arg Pro Leu Pro Val Ala Pro
1               5

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Pro Pro Pro Ala Leu Pro Pro Lys Lys Arg
1               5                   10

<210> SEQ ID NO 16
<211> LENGTH: 8
<212> TYPE: PRT
<213> ORGANISM: Artificial sequence
<220> FEATURE:
<223> OTHER INFORMATION: Synthetic peptide

<400> SEQUENCE: 16

Arg Lys Gly Asp Tyr Ala Ser Tyr
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
```

```
<400> SEQUENCE: 17

Trp Xaa Xaa Gln Phe
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa=L or R

<400> SEQUENCE: 18

Arg Xaa Leu Pro Pro Glx
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 19

Xaa Pro Pro Leu Pro Xaa Arg
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Arg Pro Leu Pro Pro Leu Pro
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa= I or V

<400> SEQUENCE: 21

Pro Pro Pro Tyr Pro Pro Pro Pro Xaa Pro
1               5                   10
```

```
<210> SEQ ID NO 22
<211> LENGTH: 4
<212> TYPE: PRT
<213> ORGANISM: Artificial sequence
<220> FEATURE:
<223> OTHER INFORMATION: Synthetic peptide

<400> SEQUENCE: 22

Gly Leu Gly Phe
1

<210> SEQ ID NO 23
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa=R or K
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa= Any Hydrophobic amino acid
<220> FEATURE:
<221> NAME/KEY: MISC_FEATURE
<222> LOCATION: (8)..(8)
<223> OTHER INFORMATION: Xaa= Any Hydrophobic amino acid

<400> SEQUENCE: 23

Xaa Xaa Xaa Xaa Gly Xaa Gly Xaa
1               5

<210> SEQ ID NO 24
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa= Any Hydrophobic amino acid
<220> FEATURE:
<221> NAME/KEY: MISC_FEATURE
<222> LOCATION: (2)..(2)
<223> OTHER INFORMATION: Xaa= K or R
<220> FEATURE:
<221> NAME/KEY: misc_feature
<222> LOCATION: (3)..(3)
<223> OTHER INFORMATION: Xaa can be any naturally occurring amino acid

<400> SEQUENCE: 24

Xaa Xaa Xaa Ser Asp Val
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa= Any Aromatic amino acid
<220> FEATURE:
<221> NAME/KEY: MISC_FEATURE
```

```
<222> LOCATION: (2)..(2)
<223> OTHER INFORMATION: Xaa= K or R
<220> FEATURE:
<221> NAME/KEY: MISC_FEATURE
<222> LOCATION: (5)..(5)
<223> OTHER INFORMATION: Xaa= S, T, K or R
<220> FEATURE:
<221> NAME/KEY: MISC_FEATURE
<222> LOCATION: (6)..(6)
<223> OTHER INFORMATION: Xaa= Any Hydrophobic amino acid

<400> SEQUENCE: 25

Xaa Xaa Glu Thr Xaa Xaa
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa= Any Hydrophobic amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Xaa Xaa Glu Thr Xaa Leu
1               5

<210> SEQ ID NO 27
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 27

Glu Thr Xaa Val
1

<210> SEQ ID NO 28
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa= Any Aromatic amino acid
<220> FEATURE:
<221> NAME/KEY: MISC_FEATURE
<222> LOCATION: (5)..(5)
<223> OTHER INFORMATION: Xaa= Any Aliphatic amino acid

<400> SEQUENCE: 28

Xaa Xaa Thr Trp Xaa
1               5

<210> SEQ ID NO 29
<211> LENGTH: 7
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: Xaa= Any Hydrophobic amino acid
<220> FEATURE:
<221> NAME/KEY: MISC_FEATURE
<222> LOCATION: (4)..(5)
<223> OTHER INFORMATION: Xaa= T or S
<220> FEATURE:
<221> NAME/KEY: MISC_FEATURE
<222> LOCATION: (6)..(6)
<223> OTHER INFORMATION: Xaa= Any Aromatic amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 29

Xaa Xaa Xaa Xaa Xaa Xaa Xaa
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa= Any Aromatic amino acid

<400> SEQUENCE: 30

Phe Asp Xaa Xaa Cys
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa= Any Aromatic amino acid
<220> FEATURE:
<221> NAME/KEY: MISC_FEATURE
<222> LOCATION: (5)..(5)
<223> OTHER INFORMATION: Xaa= Any Aliphatic amino acid

<400> SEQUENCE: 31

Trp Xaa Xaa Asp Xaa
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa= Any Aromatic amino acid
<220> FEATURE:
```

```
<221> NAME/KEY: MISC_FEATURE
<222> LOCATION: (3)..(3)
<223> OTHER INFORMATION: Xaa= Any Hydrophobic amino acid
<220> FEATURE:
<221> NAME/KEY: MISC_FEATURE
<222> LOCATION: (5)..(5)
<223> OTHER INFORMATION: Xaa= Any Aliphatic amino acid

<400> SEQUENCE: 32

Trp Xaa Xaa Asp Xaa
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa= Any Hydrophobic amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa= E or D
<220> FEATURE:
<221> NAME/KEY: MISC_FEATURE
<222> LOCATION: (5)..(7)
<223> OTHER INFORMATION: Xaa= Any Hydrophobic amino acid

<400> SEQUENCE: 33

Xaa Xaa Xaa Xaa Xaa Xaa Xaa
1               5

<210> SEQ ID NO 34
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: Xaa= Any Hydrophobic amino acid

<400> SEQUENCE: 34

Xaa Xaa Xaa Xaa
1

<210> SEQ ID NO 35
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa= D or E
<220> FEATURE:
<221> NAME/KEY: MISC_FEATURE
<222> LOCATION: (2)..(2)
<223> OTHER INFORMATION: Xaa= Any Hydrophobic amino acid
<220> FEATURE:
<221> NAME/KEY: MISC_FEATURE
<222> LOCATION: (3)..(3)
<223> OTHER INFORMATION: Xaa= Any Aromatic amino acid
<220> FEATURE:
```

```
<221> NAME/KEY: MISC_FEATURE
<222> LOCATION: (4)..(4)
<223> OTHER INFORMATION: Xaa= Any Hydrophobic amino acid

<400> SEQUENCE: 35

Xaa Xaa Xaa Xaa
1

<210> SEQ ID NO 36
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa= Any Aromatic amino acid
<220> FEATURE:
<221> NAME/KEY: MISC_FEATURE
<222> LOCATION: (3)..(3)
<223> OTHER INFORMATION: Xaa= S or T
<220> FEATURE:
<221> NAME/KEY: MISC_FEATURE
<222> LOCATION: (6)..(6)
<223> OTHER INFORMATION: Xaa= Any Aliphatic amino acid

<400> SEQUENCE: 36

Trp Xaa Xaa Asp Trp Xaa
1               5

<210> SEQ ID NO 37
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa= Any Aromatic amino acid
<220> FEATURE:
<221> NAME/KEY: MISC_FEATURE
<222> LOCATION: (2)..(2)
<223> OTHER INFORMATION: Xaa= Any Hydrophobic amino acid

<400> SEQUENCE: 37

Xaa Xaa Gly Trp Phe
1               5
```

IMMUNOTHERAPY

This application is a national phase application under 35 U.S.C. § 371 of International Application No. PCT/US2016/060513, filed on Nov. 4, 2016, which claims priority to U.S. provisional patent application Ser. No. 62/252,043, filed Nov. 6, 2015, each of which is incorporated herein by reference in its entirety

STATEMENT REGARDING FEDERALLY SPONSORED RESEARCH OR DEVELOPMENT

This invention was made with government support under grant CMBT1511720 awarded by the National Science Foundation and grants CA191952 and AI109204 awarded by the National Institutes of Health. The government has certain rights in the invention.

SEQUENCE LISTING

Incorporated by reference in its entirety herein is a computer-readable nucleotide/amino acid sequence listing submitted concurrently herewith and identified as follows: One 11,632 Byte ASCII (Text) file named "34657-252_SEQUENCE_LISTING_ST25," created on Aug. 27, 2021.

FIELD

Provided herein is technology relating to immunotherapy and particularly, but not exclusively, to compositions, methods, and kits for immunotherapy and activation of T cells.

BACKGROUND

Cellular immunotherapy uses a patient's own immune response to treat disease (e.g., infectious disease, cancer). Fundamentally speaking, a successful cellular immunotherapy relies on the function of activated T cells (e.g., cytotoxic CD8+ T cells and helper CD4+ T cells), a type of immune cell that recognizes antigenic peptides associated with a disease-causing agent (e.g., a tumor cell, a pathogen, etc.). For example, activated T cells remove cancer cells from a diseased individual by recognizing antigenic peptides from a tumor, infiltrating the tumor, recruiting other immune cells to the tumor, and destroying the cancer cells.

One aspect of the immune system is that T cells proliferate upon activation. To control the activation of T cells and prevent associated problems with an excessive immune response, T cell activity is controlled by suppressive signals in the microenvironment. However, in some instances, suppression of T cell activity leads to an insufficient number of T cells to produce an effective immune response toward the disease and, consequently, the disease state remains and may worsen.

Some therapies have been developed to boost and improve a diseased individual's immune response by infusing the individual with a large amount (e.g., $\geq 10^{10}$) of antigen-reactive T cells to supplement the innate T cell response. However, such approaches have failed to meet clinical expectations, especially for cancer therapies.

SUMMARY

Research has indicated that only a limited fraction of the infused T cells having a "young and multitasking" property (e.g., central memory and polyfunctional phenotypes) persisted and were effective to combat disease (e.g., that mediated tumor regression in a cancer patient). Based on these and other results, it was contemplated that the quality of the tumor-specific activated T cells, not solely the quantity of the tumor-specific activated T cells, plays a role in determining the clinical outcome of a T cell immunotherapeutic technology (e.g., for cancer). Accordingly, immunotherapies based on effectively activating and conditioning tumor-specific T cells with particular disease-fighting qualities would provide improved disease treatment outcomes. Furthermore, technological advancements in the field would provide insights into the molecular mechanisms of effective anti-tumor T-cell immunity and, consequently, lead to improved therapeutic technologies. Accordingly, the technology provided herein is based on discoveries relating to T cell activation and defining detailed aspects of T cell activation that provide an improved immunotherapy.

Accordingly, in some embodiments the technology relates to a composition for activating T cells comprising a primary anchor protein comprising a first anchor subunit; a dock protein comprising a first dock subunit that is an orthogonal binding partner of the first anchor subunit and a second dock subunit; and a pMHC protein comprising an antigenic peptide and a second anchor subunit that is an orthogonal binding partner of the second dock subunit. In some embodiments, the primary anchor protein is a fusion protein comprising a protein for cell surface display of the primary anchor protein (for expression on the cell surface of, e.g., a yeast cell). In some embodiments, the primary anchor protein is a fusion protein comprising a portion encoding a yeast mating protein, e.g., a fusion protein comprising a portion encoding yeast Aga2p. In some embodiments, the primary anchor protein comprises an epitope tag and/or the dock protein comprises an epitope tag (e.g., to purify, isolate, and/or detect the primary anchor protein and/or the dock protein). The technology is not limited in the epitope tag(s) used—exemplary epitope tags are, e.g., V5 and c-myc. Embodiments provide for the purification, isolation, and/or detection of the various components of the compositions (e.g., the scaffolds and protein assemblies). In exemplary embodiments, the dock protein comprises a purification tag (e.g., a histidine tag for purification by a nickel affinity column) and/or the pMHC protein comprises a purification tag (e.g., a histidine tag for purification by a nickel affinity column).

In some embodiments, the composition comprises a primary anchor protein comprising a first anchor subunit, a second anchor subunit, and a third anchor subunit; a first dock protein comprising a first dock subunit that is an orthogonal binding partner of the first anchor subunit and a fourth dock subunit; a second dock protein comprising a second dock subunit that is an orthogonal binding partner of the second anchor subunit and a fifth dock subunit; a third dock protein comprising a third dock subunit that is an orthogonal binding partner of the third anchor subunit and a sixth dock subunit; an adhesion protein comprising a fourth anchor subunit that is an orthogonal binding partner of the fourth dock subunit; a co-stimulatory protein comprising a fifth anchor subunit that is an orthogonal binding partner of the fifth dock subunit; and a pMHC protein comprising an antigenic peptide and a sixth anchor subunit that is an orthogonal binding partner of the sixth dock subunit. While the technology is not limited in the adhesion proteins that find use in the protein assemblies, exemplary embodiments comprise an adhesion protein that is ICAM1 (Intercellular Adhesion Molecule, also known as CD54 (Cluster of Differentiation 54)). Furthermore, while the technology is not limited in the co-stimulatory proteins that find use in the protein assemblies, exemplary embodiments comprise a co-stimulatory protein that is CD80 (Cluster of Differentiation 80 (also B7-1)) or CD137L (also known as 4-1BBL, CDw137L, TNFSF9). In some embodiments, the protein assemblies comprise a co-stimulatory protein that is, e.g., 4-1BBL, CD30L, CD70, or TL1A. In some embodiments, the protein assemblies comprise a coinhibitory protein that is, e.g., B7-H1 (PD-L1), or Galectin-9.

And, while the technology is not limited in the immunological synapse pattern in which the pMHC, adhesion molecule, and/or co-stimulatory protein are arranged, exemplary embodiments comprise the adhesion protein, co-stimulatory protein, and pMHC arranged in a bulls-eye pattern. Other patterns include a multifocal pattern, a polarized pattern, and a kinapse pattern. In some embodiments, the primary anchor protein is expressed by a cell; and the first dock protein, the second dock protein, the third dock protein, the adhesion protein, the co-stimulatory protein, and the pMHC protein are expressed as soluble proteins.

In additional embodiments, the technology provides a method of activating T cells comprising contacting T cells with a pMHC complex assembled on a protein scaffold. In some embodiments, the protein scaffold comprises pMHC (e.g., a peptide-MHC complex, e.g., a peptide-MHCI complex, a peptide-MHCII complex), an adhesion protein, and a co-stimulatory protein in an immunological synapse pattern. In some embodiments, the protein scaffold comprises pMHC, an adhesion protein, and a co-stimulatory protein in a bull-eye pattern. Further embodiments comprise exposing the T cells to a cytokine, e.g., a cytokine present in a natural IS for activation of T cells. In particular methods, the methods comprise assembling the protein scaffold on a host call (e.g., a yeast cell) using orthogonal pairs of anchor subunits and dock subunits and, in related embodiments, the technology comprises expressing a primary anchor protein on the surface of a cell and assembling one or more dock proteins onto the primary anchor protein to provide the protein scaffold.

The technology finds use in the treatment of a subject (e.g., a subject having a disease or at risk for disease). In some embodiments, T cells are isolated from the subject who is in need of a treatment with activated T cells. Accordingly, embodiments provide methods in which T cells are obtained from a subject in need of a treatment for a disease, e.g., the T cells are obtained from a subject having or at risk of having a cancer.

In some embodiments, the technology provides the use of a pMHC assembled on a protein scaffold to activate T cells. For example, in some embodiments the technology provides use of a protein assembly comprising pMHC, an adhesion protein, and a co-stimulatory protein to activate T cells. Some embodiments provide use of a protein assembly comprising pMHC, an adhesion protein, and a co-stimulatory protein in an immunological synapse-like pattern to activate T cells. In some embodiments, the technology finds use to prepare a medicament comprising activated T cells, to prepare a medicament comprising activated T cells for treatment of a patient having or at risk of having cancer, or to prepare a medicament comprising activated T cells for treatment of a patient having or at risk of having an infectious disease. Accordingly, in some embodiments the technology provides T cells activated by pMHC presented in an immunological synapse-like pattern on a protein scaffold for use in the preparation of a medicament, e.g., T cells activated by pMHC presented in an immunological synapse-like pattern on a protein scaffold for use in the preparation of a medicament to treat cancer.

Further embodiments provide a pharmaceutical composition comprising T cells activated according to the technology provided herein. Related embodiments provide a method of treating a subject comprising administering T cells activated according to the technology provided herein.

Some embodiments relate to kits comprising a pMHC attached to a protein scaffold and a pharmaceutical buffer for the suspension of activated T cells.

The tunable and scalable protein assemblies (TSPAs) provide several advantages for activating and expanding antigen-specific (e.g., tumor-specific) T cells. For example, in some embodiments the use of high-affinity orthogonal ligand-receptor pairs derived from biological systems (e.g., scFv antibodies, signaling receptors, and cohesins/dockerins) as the "dock subunit" and "anchor subunit" building blocks of the TSPAs provides a technology to construct elaborate addressable protein scaffolds (see, e.g., FIG. 1) upon which to build the TSPAs. The number, order, and arrangement of the anchor subunits and dock subunits in the protein scaffold (and thus of the T cell activating ligands in the protein assemblies) are controlled, in some embodiments, via the manipulation of DNA sequences encoding anchor and dock subunits, thus providing a system to create molecular patterns with a precision and reproducibility that is improved relative to other current surface-patterning methods, such as photolithography. For instance, in some embodiments components of the TSPAs are positioned 1 to 10 nm (e.g., approximately 5 nm) apart from each other. Furthermore, the orthogonality of the dock subunit-anchor subunit interaction provides a modular flexibility to construct protein scaffold patterns to form different IS structures with customized formulation and arrangement of T cell-activating ligands. For example, several different IS patterns have been identified under different T-cell activating conditions. The various IS patterns induce specific T cell functions and thus expand the T cell functional space that is provided by the technology provided herein. Compared to current existing artificial antigen presentation designs, embodiments of the technology provided herein provide patterned multi-component protein presentation for effective T cell activation, expansion, and functional conditioning. The technology is contemplated to provide a similar T cell activation as provided by the extraordinarily sensitive and potent activation of T cells by the natural IS (e.g., which induces a T cell activation response to a single antigenic peptide).

As described herein, embodiments of the addressable protein scaffold combine certain advantages of a cellular system (e.g., reproducibility) with advantages of an acellular system (e.g., precise and flexible control of artificial antigen presentation). Therefore, the technology finds use in some embodiments as a high-throughput screening platform, e.g., to evaluate the contributions of each of a multitude of signals for T cell activation, expansion, phenotype, and function. Additionally, by providing different protein formulations on the scaffold, the technology is readily applicable to studying other immune cells, such as B cells, NK cells, and macrophages, and other immune-modulating diseases.

The peptide-MHC (pMHC) complex provides a key signal for T cell activation and determines the specificity of the induced T cell response. However, the soluble expression of MHC protein, especially class II (MHCII), has proven to be challenging. The insect expression system for MHCII proteins used in embodiments of the technology provides rapid peptide exchange, protein purification, and non-fluorophore-based magnetic enrichment, and thus finds use in other highly multiplexed instruments, such as mass cytometry.

An extensive number of pMHC complexes finds use in embodiments of the technology. For example, embodiments comprise pMHC complexes comprising major human MHCI and MHCII alleles such as, e.g., A*0201, B*0702, DR*0101, DR*0401, DR*0701, and DR*1501, which provide coverage of nearly 50% of the Caucasian population. In addition, embodiments provide expression of MHC in a configuration that provides for their rapid exchange into tumor-associated antigenic peptides. Accordingly, the technology finds use to study tumor-specific T cells from cancer patients. The technology also addresses concerns regarding the limited applicability of cancer immunotherapy due to the high polymorphic and polygenic nature of MHC proteins, as well as regarding the dynamic and heterogeneous nature of tumor antigens.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1: To recapitulate this patterned signal presentation using TSPAs, the technology provides an addressable protein scaffold (e.g., in a cell-surface-displayed format, a soluble format, on a solid support, etc.) using a primary anchor protein (e.g., comprising a plurality of anchor subunits), e.g., expressed as a yeast surface protein or as a soluble protein, a plurality of dock proteins (e.g., comprising a plurality of dock subunits), and a plurality of T cell-activating ligands fused to anchor subunits. In embodiments shown in FIG. 1B, the technology comprises a cell-surface-displayed format. In some embodiments, the protein scaffold comprises a primary anchor protein for anchorage and assembly of a plurality of dock proteins (e.g., 6 dock proteins, e.g., as represented by the 6 columns in the protein scaffold shown in FIG. 1). Embodiments provide orthogonal high-affinity dock-anchor pairs to provide the building blocks of the scaffold, e.g., in some embodiments to provide a self-assembling bull's eye docking scaffold. The assembly mechanism directs the T cell-activating protein ligands, each fused to a unique anchor subunit, to pair with distinct dock subunits in the addressable protein scaffold forming an artificial IS for effective antigen presentation. The peptide-MHC complex (pMHC), CD80, and ICAM1 are among the best-characterized T-cell-activating ligands.

FIG. 8A is a schematic representation of the scaffold comprising an $(aA1)_1$ (top) or $(aA1)_2$ (bottom) protein tagged with a V5 epitope and a soluble $dA1$-$(dA2)_4$ protein tagged with a Cmyc epitope. FIG. 8B is flow cytometry data collected from yeast cells displaying the scaffold and that were co-stained with anti-V5 and anti-Cmyc antibodies. The parallel staining pattern of the $(aA1)_2$-$dA1$-$(dA2)_4$ (upper left cloud of data points) and $(aA1)$-$dA1$-$(dA2)_4$ (lower right cloud of data points) indicates the successful assembly of the 2D scaffold with the design shown in FIG. 8A.

FIG. 9A shows a gel shift assay indicating biotinylation of the MHCI proteins. The biotinylated A2 (FIG. 9B) and B7 (FIG. 9C) proteins were exchanged with a binding EBV epitope, and then tested for staining of PBMCs from healthy donors. The double positive events in the upper-right Q2 quadrant demonstrate the specific binding of antigen-specific T cells.

FIG. 10A shows a gel shift assay indicating a >90% biotinylation of the MHCII proteins. FIGS. 10B to 10E show that the biotinylated CLIP-DR proteins were exchanged with a binding epitope from different viruses, including influenza (HA, NP, M1, and PB1) and EBV, and then tested for staining of PBMCs from healthy donors. Due to the low frequency of CD4+ T cells, several peptides were pooled for a particular allele as indicated by the subscript "m" of a viral protein. In addition, for DR4 and DR7, the same pMHC complexes were labeled with two different fluorophores. For example, DR4-PB1-specific T cells showed a double staining of APC and BV (brilliant violet) in FIG. 10D.

FIG. 11A shows an SDS-PAGE gel of the pMHC-aA2 fusion protein showing two subunits with expected sizes; FIG. 11 B shows data from yeast cells displaying the $(dA2)_n$-$(pMHC)_n$ supramolecular complexes and costained with anti-V5 (for scaffold $(dA2)_n$ display level) and anti-His (for pMHC display level) antibodies. The parallel staining pattern indicated the successful assembly of the $(dA2)_n$-$(pMHC)_n$ supramolecular complexes, which is further confirmed using fluorescence quantification beads as shown in FIG. 11C.

Figure 1A:
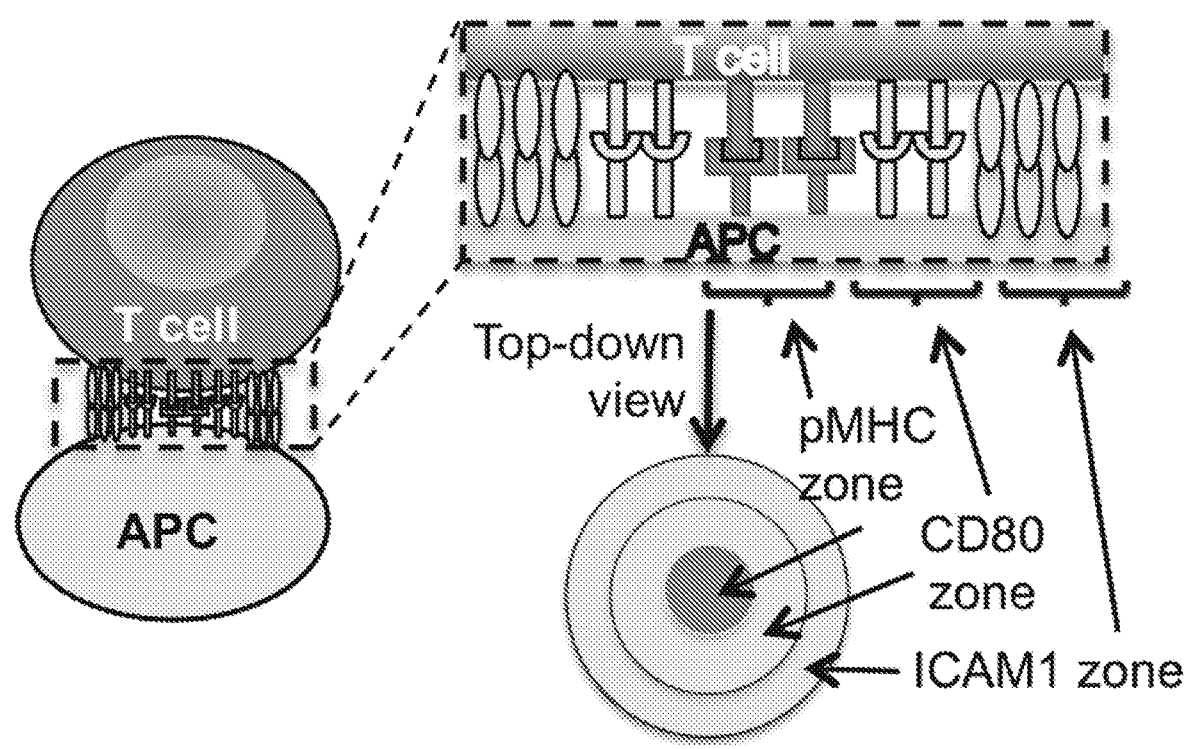
FIG. 1A: In a natural IS during T-cell activation, multiple ligand-receptor interactions occur (cross sectional view on top), and more importantly, they segregate into distinct zones forming a "bull's eye" pattern (top-down view at bottom).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to immunotherapy and particularly, but not exclusively, to compositions, methods, and systems for immunotherapy and activation of T cells.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide that possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include transmembrane domains, glycosylation sites, binding domains, kinase domains, and excretion signals.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and 5 includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include 20 sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "allele" refers to different variations in a gene; the variations include but are not limited to variants and mutants, polymorphic loci and single nucleotide polymorphic loci, frameshift and splice mutations. An allele may occur naturally in a population, or it might arise during the lifetime of any particular individual of the population.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F' (ab)2, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, inflammation, etc.).

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive vs. conventional treatment).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "pharmaceutical composition" refers to the combination of an active agent with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject.

As used herein, "carriers" include pharmaceutically acceptable carriers, excipients, or stabilizers which are non-toxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "patient" or "subject" refer to organisms to be treated by the compositions of the present technology or to be subject to various tests provided by the technology. The term "subject" includes animals, preferably mammals, including humans. In a preferred embodiment, the subject is a primate. In an even more preferred embodiment, the subject is a human.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. As used herein, "cancer therapy" and "cancer treatment" are synonymous terms. As used herein, "chemotherapy" and "chemotherapeutic" and "chemotherapeutic agent" are synonymous terms.

As used herein a "primary anchor protein" comprises one or more anchor subunits and a "dock protein" comprises one or more dock subunits.

As used herein, "orthogonal pair" refers to a pair of biomolecules (e.g., nucleic acids, proteins or domains of proteins) that specifically bind to each other. The binding between the two members of an orthogonal pair is mutually exclusive such that each member of the orthogonal pair does not specifically bind to any member of another orthogonal pair. Each member of an orthogonal pair is the "orthogonal binding partner" of the other member of the orthogonal pair. In some embodiments, an orthogonal pair comprises, consists of, or consists essentially of one anchor subunit and one dock subunit.

As used herein, the term "specifically binds" refers to binding that has a $K_d$ of approximately $10^{-9}$ to $10^{-12}$ M or stronger (e.g., having a $K_d$ less than $10^{-12}$ M).

As used herein, the term "High Five cells" refers to an insect cell line that is officially called BTI-TN-5B1-4. High Five cells originated from the ovarian cells of the cabbage looper, *Trichoplusia ni*. It was developed by the Boyce Thompson Institute for Plant Research, Ithaca, NY. High Five find use for recombinant protein expression, e.g., using baculovirus or transfection. They can be grown in the absence of serum, and can be cultured in a loose attached state or in suspension.

As used herein, the terms "immunogen" and "antigen" refer to an agent (e.g., a microorganism (e.g., bacterium, virus or fungus), a tumor cell, and/or portion or component thereof (e.g., a tumor-associated antigen)) that is capable of eliciting an immune response in a subject (e.g., capable of activating a T cell).

As used herein, the term "at risk for disease" refers to a subject that is predisposed to experiencing a particular disease (e.g., a cancer). This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present technology be limited to any particular risk (e.g., a subject may be "at risk for disease" simply by being exposed to and interacting with other people), nor is it intended that the present technology be limited to any particular disease.

As used herein, the term "T cell" refers to natural T cells (e.g., isolated from an organism, e.g., a mammal, e.g., a human, e.g., a subject), T cells grown ex vivo, and genetically engineered T cells (e.g., T cells modified using a Cas9 ribonucleoprotein delivery method). The term T cell refers both to T cells comprising a T cell receptor and to T cells comprising an artificial T cell receptor (e.g., CAR-T cells).

The terms "protein" and "polypeptide" refer to compounds comprising amino acids joined via peptide bonds and are used interchangeably. Conventional one and three-letter amino acid codes are used herein as follows—Alanine: Ala, A; Arginine: Arg, R; Asparagine: Asn, N; Aspartate: Asp, D; Cysteine: Cys, C; Glutamate: Glu, E; Glutamine: Gln, Q; Glycine: Gly, G; Histidine: His, H; Isoleucine: Ile, I; Leucine: Leu, L; Lysine: Lys, K; Methionine: Met, M; Phenylalanine: Phe, F; Proline: Pro, P; Serine: Ser, S; Threonine: Thr, T; Tryptophan: Trp, W; Tyrosine: Tyr, Y Valine: Val, V. As used herein, the codes Xaa and X refer to any amino acid.

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. Degenerate codes for nucleotides are: R (G or A), Y (T/U or C), M (A or C), K (G or T/U), S (G or C), W (A or T/U), B (G or C or T/U), D (A or G or T/U), H (A or C or T/U), V (A or G or C), or N (A or G or C or T/U), gap (–).

DESCRIPTION

T-cell activation and function are determined by signals delivered from antigen presenting cells (APCs). Due to the high cost and difficulty of manipulating a patient's own APCs (e.g., dendritic cells), some current technologies comprise use of artificial APCs (aAPCs) to activate and expand antigen-specific (e.g., tumor-specific) T cells in vitro, followed by transfer of antigen-specific (e.g., tumor-specific) T cells into patients (e.g., cancer patients). In these technologies, the aAPC system comprises cell-sized particles (either cellular or acellular) comprising protein ligands on the surface to engage and activate T cells. A variety of aAPC systems have been developed using various cell lines, polystyrene beads, and liposomes. While these current technologies have improved our understanding of what ligands are required for T cell activation and demonstrated promising results showing activation and expansion of antigen-specific T cells, the clinical outcomes of extant technologies have been disappointing.

Current aAPC designs have several technological deficiencies. First, the cellular aAPC systems do not provide adequate mechanisms to regulate expression levels of the T cell-activating proteins and to control their spatial distribution in a live cell membrane. Second, the acellular aAPC systems are generated by a random coating process to co-immobilize T cell-activating proteins to a substrate and thus also do not provide adequate spatial control of the T cell-activating proteins. In sum, the existing cellular and acellular technologies both present T cell-activating protein ligands without spatial organization.

In contrast, recent studies in T cell biology indicated that an array of receptor-ligand pairs at the T cell/APC interface, termed the "immunological synapse" (IS), cluster into distinct domains to form various patterns. (See, e.g., FIG. 1A). This highly ordered supramolecular IS structure provides ultra-sensitive T cell activation by as few as one single antigenic peptide (e.g., in a pMHC complex). Accordingly, provided herein is a technology for patterned signal presentation of T cell activating ligands (e.g., antigenic peptides) to T cells for improved T cell activation and improved cancer immunotherapy.

The technology not only provides presentation of specific ligands to T cells for their specific activation toward the ligands, but also provides for presenting the ligands to T cells in a particular pattern that improves the T cell activation. In particular, the technology comprises novel approaches in various embodiments of using protein assemblies to recapitulate one or more supramolecular patterns present in natural immunological synapses for improved T cell antigen presentation (See, e.g., FIG. 1). In addition to providing control of the spatial organization of T cell-activating ligands, the technology also provides tunable and scalable protein assemblies to accommodate patient-to-patient variability and affordability. In sum, provided herein is a technology comprising various embodiments related to tunable and scalable protein assemblies (TSPAs) for improved T-cell activation. In some embodiments, the technology finds use to engineer inexpensive and effective personalized immunotherapy, e.g., for cancer, infectious disease, or other disease.

Embodiments comprise the use of protein engineering technologies to produce an addressable protein scaffold to recapitulate (e.g., mimic, simulate, etc.) the activation of T cells via patterned signal presentation by APCs (FIG. 1A). In some embodiments, the addressable protein scaffold comprises a primary anchor protein (e.g., comprising one or more (e.g., 1, 2, 3, 4, 5, 6, 7, 8, 9, 10, or more) anchor subunits) and one or more (e.g., 1, 2, 3, 4, 5, 6, 7, 8, 9, 10, or more) dock proteins (e.g., each comprising one or more (e.g., 1, 2, 3, 4, 5, 6, 7, 8, 9, 10, or more) dock subunits) that are assembled together, e.g., using a combination of recombinant engineered proteins (e.g., genetic fusions) (e.g., the primary anchor protein and the dock proteins indicated by the columns in FIG. 1) and high-affinity protein-protein interactions between anchor subunits and dock subunits (e.g.., bi-directional arrows in FIG. 1).

Embodiments of the technology provide orthogonal pairs of interacting proteins. For example, in some embodiments each dock subunit binds only one type of T cell-activating ligand through specific protein-protein interactions with an anchor subunit fused to the T cell-activating ligand. In this way, each ligand is assigned a unique address on the protein scaffold. Accordingly, the spatial arrangement of the ligands is precisely controlled by genetic manipulation of the dock subunits within each dock protein and the primary anchor protein that holds the dock proteins, and thus the dock subunits, in the appropriate pattern.

T cells recognize disease causing agents (e.g., cancer cells, pathogens) by binding antigenic peptides (e.g., tumor-associated antigenic peptides) that are associated with major histocompatibility complexes ("MHC") in peptide-MHC complexes ("pMHC") via surface T cell receptors ("TCR"). The MHC proteins are very diverse as a result of being polygenic (encoded by multiple genes in each person), codominant (expressed from both alleles of a gene), and highly polymorphic (having genetic variation among people). In addition, tumor-associated antigenic peptides are highly heterogenous and dynamic in the process of tumor progression, as well as during tumor regression after the immunotherapy.

Accordingly, the addressable protein scaffolding technology provided herein finds use in presenting any desired peptide-MHC combination for an individual patient and for different disease stages of the same patient, thus providing a personalized cancer immunotherapy. Embodiments of the technology provide for easily exchanging one ligand in the TSPA with another ligand or with another version of the same ligand, such as one or more other (e.g., different) peptide-MHC complexes. Moreover, embodiments of the technology provide for the expression of any peptide-MHC construct, e.g., some embodiments provide peptide-MHC constructs comprising the major MHC alleles expressed by at least 50% of the Caucasian population, which are rapidly loaded with any desired peptides to form a functional peptide-MHC complex.

In some embodiments, the TSPAs comprise recombinant proteins expressed using eukaryotic expression systems (e.g., yeast cells, insect cells, etc.). The yeast and insect cell systems are known in the art as robust host organisms for large-scale biomanufacturing of proteins (e.g., complex therapeutic proteins). Accordingly, embodiments of the technology comprising use of the TSPAs provide an accessible and inexpensive platform for providing personalized cancer immunotherapy according to embodiments of the technology provided herein.

In various embodiments, the TSPAs are produced in different formats. In exemplary embodiments, the TSPAs are produced in a soluble form or as displayed on the surface of a cell (e.g., a yeast cell (see, e.g., FIG. 1)). While the soluble form is desirable in some embodiments for clinical application of cancer immunotherapy, the cell-surface form is amenable in some embodiments for design and engineering of any TSPA configuration using high-throughput molecular and/or cellular techniques, including, for example, screening of different T cell-activating protein ligands, creating addressable protein scaffolds with different patterns, and flow cytometry. In some embodiments, the cell-surface form is amenable for testing TSPA configurations, e.g., to identify improvements in performance and efficiency of the technology (e.g., in some embodiments, to identify a minimal and/or optimal TSPA configuration for presentation of antigenic peptides and T cell activation). In some embodiments, the TSPAs are provided on a solid support, e.g., on a bead.

Tunable and scalable protein assemblies Embodiments of the technology provide tunable and scalable protein assemblies (TSPAs) that find use in embodiments of the technology related to providing personalized immunotherapy, e.g., for treating a disease such as, e.g., cancer, infectious disease, or other diseases. In some embodiments, the TSPAs are designed and engineered to comprise particular T cell-activating components and/or ligands. For example, in some embodiments, the TSPAs comprise particular peptides in the pMHC complexes. In some embodiments, the TSPAs comprise other T cell-activating ligands such as, e.g., CD80, ICAM1, etc. In some embodiments, the TSPAs comprise a particular pattern of pMHC. In some embodiments, the TSPAs comprise a particular pattern of pMHC and other T cell activating ligands such as, e.g., CD80, ICAM1, etc. In some embodiments, the TSPAs are designed and engineered to provide a "bull's eye" immunological synapse pattern, e.g., a pattern comprising pMHC in the center, which is surrounded by an inner ring of CD80, and which is further surrounded by an outer ring of ICAM1 (see, e.g., FIG. 1A). In some embodiments, TSPAs comprise pMHC and one or more T cell activating ligands such as, e.g., CD80, ICAM1, CD40, CD86, ICOSL, GITRL, OX40L, etc. (see, e.g., Grewal, I. S.; Flavell, R. A.: The role of CD40 ligand in costimulation and T-cell activation. Immunological reviews 1996, 153, 85-106; Freeman, G. J.; Borriello, F.; Hodes, R. J.; Reiser, H.; Gribben, J. G.; Ng, J. W.; Kim, J.; Goldberg, J. M.; Hathcock, K.; Laszlo, G.: Murine B7-2, an alternative CTLA4 counter-receptor that costimulates T cell proliferation and interleukin 2 production. The Journal of experimental medicine 1993, 178, 2185-92; Thomas, I. J.; Petrich de Marquesini, L. G.; Ravanan, R.; Smith, R. M.; Guerder, S.; Flavell, R. A.; Wraith, D. C.; Wen, L.; Wong, F. S.: CD86 has sustained costimulatory effects on CD8 T cells. J Immunol 2007, 179, 5936-46; Chattopadhyay, K.; Bhatia, S.; Fiser, A.; Almo, S. C.; Nathenson, S. G.: Structural basis of inducible costimulator ligand costimulatory function: determination of the cell surface oligomeric state and functional mapping of the receptor binding site of the protein. J Immunol 2006, 177, 3920-9; Shevach, E. M.; Stephens, G. L.: The GITR-GITRL interaction: co-stimulation or contrasuppression of regulatory activity? Nature reviews. Immunology 2006, 6, 613-8; Piao, J.; Kamimura, Y.; Iwai, H.; Cao, Y.; Kikuchi, K.; Hashiguchi, M.; Masunaga, T.; Jiang, H.; Tamura, K.; Sakaguchi, S.; Azuma, M.: Enhancement of T-cell-mediated anti-tumour immunity via the ectopically expressed glucocorticoid-induced tumour necrosis factor receptorrelated receptor ligand (GITRL) on tumours. Immunology 2009, 127, 489-99; and Mendel, I.; Shevach, E. M.: Activated T cells express the OX40 ligand: requirements for induction and costimulatory function. Immunology 2006, 117, 196-204.), each of which is incorporated herein by reference).

In some embodiments, TSPAs comprise one or more costimulatory proteins (e.g., 4-1BBL, CD30L, CD70, TL1A) and/or one or more coinhibitory Molecules (e.g., B7-H1 (PD-L1), Galectin-9).

During the development of embodiments of the technology, TSPAs are tested in experiments to investigate the relationship between the composition of the T cell-activating ligands in the TSPA, the pattern of the ligands, and the anti-tumor activity of the T cells activated and/or expanded with the TSPA. Further, during the development of embodiments of the technology, TSPAs and related technologies are tested to identify appropriate compositions and patterns for T cell based personalized immunotherapy engineering (e.g., to identify a minimal and/or optimal TSPA composition and/or pattern).

Figure 1B:
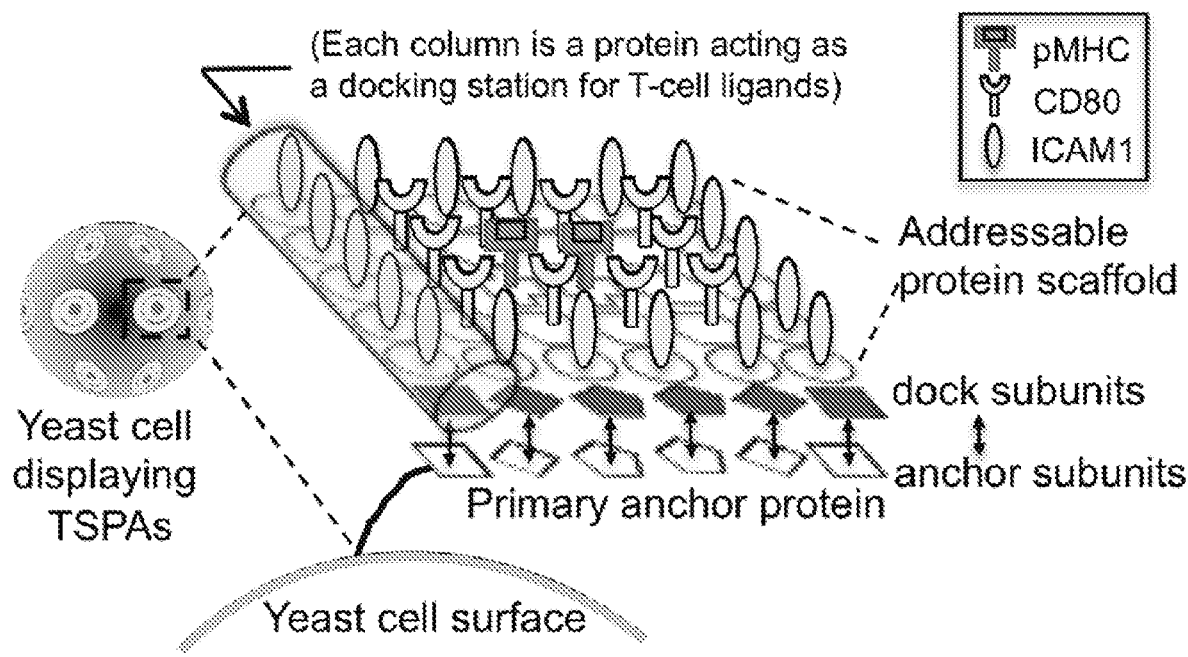
FIG. 1 is a schematic showing the design of some embodiments of the tunable and scalable protein assemblies (TSPAs) provided herein for presenting T cell-activating protein ligands in a defined pattern (e.g., a "bulls-eye" pattern) as present in a natural immunological synapse (IS).

Embodiments of the technology provide TSPAs, e.g., comprising: 1) an addressable protein scaffold; and 2) T cell-activating proteins (e.g., peptide-MHC (pMHC) complexes, co-stimulatory molecule CD80, adhesion molecule ICAM1, CD40, CD86, ICOSL, GITRL, OX40L, etc.). In some embodiments, the technology comprises a TSPA comprising pMHC complexes, co-stimulatory molecule CD80, and adhesion molecule ICAM1 in a bull's eye pattern, e.g., as shown in FIG. 1B. The addressable protein scaffold further comprises one or more (e.g., 1, 2, 3, 4, 5, 6, 7, 8, 9, 10, or more) primary anchor proteins and one or more (e.g., 1, 2, 3, 4, 5, 6, 7, 8, 9, 10, or more) dock proteins; and, a primary anchor protein further comprises one or more (e.g., 1, 2, 3, 4, 5, 6, 7, 8, 9, 10, or more) anchor subunits and each dock protein further comprises one or more (e.g., 1, 2, 3, 4, 5, 6, 7, 8, 9, 10, or more) dock subunits. The T cell-activating proteins are linked to an anchor subunit to provide a specific interaction with a specific dock subunit in the scaffold.

Embodiments of the technology comprise and/or provide an addressable protein scaffold. In some embodiments, the addressable protein scaffold is provided by expressing and displaying one or more (e.g., 1, 2, 3, 4, 5, 6, 7, 8, 9, 10, or more) primary anchor proteins on the surface of a cell (e.g., the surface of a bacterial cell, the surface of a eukaryotic cell (e.g., yeast cell surface, insect cell surface)). One or more (e.g., 1, 2, 3, 4, 5, 6, 7, 8, 9, 10, or more) dock proteins, each comprising one or more (e.g., 1, 2, 3, 4, 5, 6, 7, 8, 9, 10, or more) dock subunits, assemble by interaction of dock subunits with anchor subunits to form the protein scaffold. In some embodiments, the addressable protein scaffold is provided on a solid support (e.g., a bead, a planar surface), e.g., one or more (e.g., 1, 2, 3, 4, 5, 6, 7, 8, 9, 10, or more) primary anchor proteins and/or dock proteins are provided on a solid support. In some embodiments, the addressable protein scaffold is provided in a soluble form, e.g., one or more (e.g., 1, 2, 3, 4, 5, 6, 7, 8, 9, 10, or more) primary anchor proteins are provided and one or more (e.g., 1, 2, 3, 4, 5, 6, 7, 8, 9, 10, or more) dock proteins are provided and assembled in solution.

Each primary anchor protein comprises one or more (e.g., 1, 2, 3, 4, 5, 6, 7, 8, 9, 10, or more) anchor subunits. In some embodiments, an anchor subunit of the primary anchor protein interacts with a dock subunit of a dock protein. Some embodiments provide one or more (e.g., 1, 2, 3, 4, 5, 6, 7, 8, 9, 10, or more) dock proteins, each dock protein comprising one or more (e.g., 1, 2, 3, 4, 5, 6, 7, 8, 9, 10, or more) dock subunits that bind unique anchor subunits of the primary anchor protein according to the orthogonal dock subunit-anchor subunit pairings provided herein. That is, embodiments of the technology comprise orthogonal pairs of anchor subunits and dock subunits that bind each other with high affinity (e.g., having a $K_d$ of approximately $10^{-9}$ to $10^{-12}$ M or stronger) (see, e.g., FIG. 1B, double arrows).

The technology is not limited in the dock subunit-anchor subunit pairs that find use in the technology. Several exemplary orthogonal dock subunit-anchor subunit pairs find use and/or are contemplated by embodiments of the technology. For example, exemplary dock subunit-anchor subunit pairs that find use in embodiments of the technology are derived from natural ligand-receptor pairs (see, e.g., Dueber, J. E.; Wu, 25 G. C.; Malmirchegini, G. R.; Moon, T. S.; Petzold, C. J.; Ullal, A. V.; Prather, K. L.; Keasling, J. D.: Synthetic protein scaffolds provide modular control over metabolic flux. Nature biotechnology 2009, 27, 753-9; Bayer, E. A.; Lamed, R.; White, B. A.; Flint, H. J.: From cellulosomes to cellulosomics. Chem Rec 2008, 8, 364-77; Fontes, C. M.; Gilbert, H. J.: Cellulosomes: highly efficient nanomachines designed to deconstruct plant cell wall complex carbohydrates. Annual review of biochemistry 2010, 79, 655-81; and Morais, S.; Barak, Y.; Caspi, J.; Hadar, Y.; Lamed, R.; Shoham, Y.; Wilson, D. B.; Bayer, E. A.: Cellulase-xylanase synergy in designer cellulosomes for enhanced degradation of a complex cellulosic substrate. mBio 2010, 1, each incorporated herein by reference), e.g., scFv antibodies, signaling receptors, and cohesins (e.g., a cohesin-dockerin interaction; see, e.g., Bayer et al. (2004) "The cellulosomes: multienzyme machines for degradation of plant cell wall polysaccharides" Annu Rev Microbiol. 58: 521-54; Zverlov et al. (2008) "Mutations in the Scaffoldin Gene, cioA, of *Clostridium thermocellum* with Impaired Cellulosome Formation and Cellulose Hydrolysis: Insertions of a New Transposable Element, IS1447, and Implications for Cellulase Synergism on Crystalline Cellulose" J Bacteriol. 190(12): 4321-4327, each incorporated herein by reference). Dock subunit-anchor subunit pairs mediate the interaction between the primary anchor protein and the dock protein(s) and dock subunit-anchor subunit pairs mediate the interaction between the dock protein(s) and the T cell activating ligands. Accordingly, the dock subunit-anchor subunit pairs provide for the self-assembly of the protein scaffold (e.g., a two-dimensional scaffold) and the assembly of the T cell-activating components bound on the protein scaffold in a particular pattern (e.g., a bull's eye pattern).

For example, in some embodiments the following orthogonal interacting pairs find use in the technology. The two members of each exemplary orthogonal pair find use as an anchor subunit and dock subunit, respectively, or as a dock subunit and anchor subunit, respectively, in various embodiments of the technology.

1. Cohesin/Dockerin Pairs

In some embodiments, a cohesin (e.g., a cohesin module or cohesin domain) and a dockerin (e.g., a dockerin module or dockerin domain) provide one or more of the interacting orthogonal pairs of anchor subunits and dock subunits. A cohesin domain is a protein domain of a cohesin protein that specifically binds to a dockerin domain of a dockerin protein. Dockerin domains are highly conserved and typically comprise approximately 60 to 80 (e.g., 65 to 70) amino acids. Cohesin-dockerin interactions produce the formation of a structure called the cellulosome in cellulolytic bacteria. In particular, the scaffoldin component of the cellulolytic bacterium *Clostridium thermocellum* is a non-hydrolytic protein that organizes the cellulolytic enzymes into a large complex, called the cellulosome. Scaffoldin comprises a plurality of cohesin domains that integrate the individual enzymatic subunits into the complex.

Cohesin domains are provided by accession number IPR002102 at the InterPro website and are identified in the Pfam database by accession PF00963 (Pfam clan CL0203); In addition, the SCOP database describes cohesins at accession lanu (e.g., Superfamily lanu) and the CDD identifier is cd08546.

Dockerin domains are provided by accession number IPR002105 at the InterPro website and are identified in the Pfam database by accession PF00404. The PROSITE database describes dockerins at accession number PDOC00416, SCOP at ldaq (e.g., Superfamily ldaq) and the CDD identifier is cd14253.

Cohesin domains and dockerin domains are conserved across dockerin and cohesin proteins from different organisms. In addition, dockerin domains and cohesin domains are classified into three groups: dockerin domain types I, II and III bind to cohesin domain types I, II and III, respectively.

For example, embodiments comprise the following interacting cohesin-dockerin pairs: *C. thermocellum* CipA Coh1 and CelS; *C. thermocellum* CipA Coh2 and CelS; *C. thermocellum* CipA Coh3 and CelS; *C. cellulolyticum* CipC and CelCCA; *Ruminococcus flavefaciens* ScaB and ScaA; and *C. thermocellum* OlpB and OlpB.

In some embodiments, a portion (e.g., a domain, e.g., a Coh1, Coh2, or Coh3 domain) of the CipA protein from *Clostridium thermocellum* (e.g., strain DSM 1237 (corresponding to ATCC 27405, JCM 12338, and NCIB 10682; and having a genome sequence provided by GenBank accession no. CP000568, incorporated herein by reference) forms an orthogonal pair with a CelS protein (also known as a Cel48A protein). CipA (cellulosome-integrating protein A) is a scaffold in protein encoded by the cipA gene from *C. thermocellum*. *C. thermocellum* CipA comprises nine type I cohesin modules (e.g., identified as Coh1, Coh2, Coh3, Coh4, Coh5, Coh6, Coh7, Coh8, and Coh9) to which enzymes and other protein components specifically bind by virtue of type I dockerin modules. Zverlov, cited above, provides methods for the cloning and expression of the cipA gene. Wild-type CipA amino acid sequences are provided by the genome sequence of *C. thermocellum* ATCC27405 (accession number YP_001039466) and *C. thermocellum* DSM 1313 (accession number ADU73707). Jindou et al. (2004) "Cohesin-Dockerin Interactions within and between *Clostridium josui* and *Clostridium thermocellum*" J. Biological Chemistry 279(11): 9867-9874, which is incorporated herein by reference, provides methods for cloning cohesin modules (e.g., Coh1, Coh2, and/or Coh3) from the cipA gene of *C. thermocellum*. The sequences of clostridial scaffoldin genes are provided, e.g., by Gerngross, et al. (1993) "Sequencing of a *Clostridium thermocellum* gene (cjpA) encoding the cellulosomal SL-protein reveals an unusual degree of internal homology" Mol. Microbiol. 8:325-334; Kakiuchi et al (1998) "Cloning and DNA sequencing of the genes encoding *Clostridium josui* scaffolding protein CipA and cellulase CelD and identification of their gene products as major components of the cellulosome." J. Bacteriol. 180:4303-4308; Pagés et al. (1999) "Sequence analysis of scaffolding protein CipC and ORFXp, a new cohesin-containing protein in *Clostridium cellulolyticum*: comparison of various cohesin domains and subcellular localization of ORFXp" J. Bacteriol. 181:1801-1810; and Shoseyov et al (1992) "Primary sequence analysis of *Clostridium cellulovorans* cellulose binding protein A" Proc. Natl. Acad. Sci. USA 89:3483-3487, which are incorporated herein by reference.

Lytle et al. (1996) J. Bacteriol. 178, 1200-1203, incorporated herein by reference, describes plasmids (e.g., referred to by the names pR1, pR2, and pR3 therein) comprising DNA fragments encoding the first, second, and third cohesin domains (e.g., Coh1, Coh2, and Coh3) from *C. thermocellum*.

The nucleotide and amino acid sequences of known cohesin proteins, cohesin domains, dockerin proteins, and dockerin domains find use in identifying other cohesin proteins, cohesin domains, dockerin proteins, and dockerin domains in nucleotide sequences and amino acid sequences available in databases or as provided by nucleotide or amino acid sequences obtained by any method. For example, alignment of sequences may be conducted by the local homology algorithm of Smith and Waterman (e.g., Smith and Waterman, Adv. Appl. Math. 2: 482 (1981)), by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988)), by computerized implementations of these algorithms (GAP, BESTFIT, FASTA, and TFASTA, e.g., as provided by the Wisconsin Genetics Software Package Release 7.0, Genetics Computer Group, 575 Science Dr., Madison, Wis.), or by visual inspection by one of ordinary skill in the art. In some embodiments, NCBI blastp, blastn, and/or HomoloGene are used.

In some embodiments, the technology comprises use of cohesin and dockerin modules from related genes in other clostridial bacteria (e.g., the cipC gene encoding the CipC protein in *C. cellulolyticum*; the cbpA gene encoding the CbpA protein in *C. cellulovorans*, and the cipA gene encoding the CipA protein in *C. josui*). For example, in some embodiments, the gene sdbA encodes a protein SdbA that specifically binds the dockerin domain of CipA.

In some embodiments, the technology comprises use of the *C. cellulolyticum* CipC (e.g., NCBI accession WP_015924274) and CelCCA (e.g., NCBI accession WP_015924614). In some embodiments, the technology comprises use of the *C. thermocellum* OlpB cohesin having an accession number WP_020458018 and an OlpB dockerin or a CipA dockerin having an accession number WP_020458017.

Accordingly, the technology comprises use of cohesin and dockerin domains from clostridia and other bacteria within and outside of the *Clostridium* genus.

For example, outside the *Clostridium* genus, organisms in the genus *Ruminococcus* (e.g., *Ruminococcus flavefaciens*) comprise cohesin-dockerin pairs. Accordingly, in some embodiments cohesin-dockerin pairs from *Ruminococcus flavefaciens* find use in the technology provided herein. In some embodiments, ScaB and ScaA proteins (encoded by scaBand scaA genes, respectively) find use in the present technology as an orthogonal pair. Ding et al. (2001). "Cellulosomal scaffoldin-like proteins from *Ruminococcus flavefaciens*", J Bacteriol 183 (6): 1945-53, which is incorporated herein by reference, provides methods for cloning and expressing cohesin and dockerin domains from ScaB and ScaA proteins. Both proteins contain multiple copies of cohesin domains, and ScaA contains a dockerin domain. For example, in some embodiments the technology comprises use of a cohesin domain from ScaA and/or ScaB and a dockerin from ScaA.

In some embodiments, proteins (e.g., portions thereof) having GenBank or Swiss-Prot accession numbers for scaffoldins that find use include, e.g., the primary scaffoldin, CipA (Q06851), and anchoring scaffoldins, SdbA (U49980), OlpB (Q06852), and Orf2p (Q06853) from *C. thermocellum*; ScaA and ScaB (AF224509) from *B. cellulosolvens*; ScaA (AF155197), ScaB (AY221112), and ScaC (AY221113) from *A. cellulolyticus* and CipC (U40345) from *C. cellulolyticum*.

2. SH3 Ligand/SH3 Domain Pairs

In some embodiments, an SH3 ligand and an SH3 domain provide one or more of the interacting orthogonal pairs of anchor subunits and dock subunits. The SH3 (SRC "sarcoma" Homology 3) domain is a small protein domain of approximately 60 amino acids that is present as a conserved sequence in many proteins, e.g., in the viral adaptor protein v-Crk; phospholipase; several cytoplasmic tyrosine kinases such as Abl and Src, PI3 kinase; Ras GTPase-activating protein; CDC24; and cdc25. Approximately 300 SH3 domains are found in proteins encoded in the human genome. SH3 domain sequences are identifiable, e.g., in various databases, e.g., in Pfam at accession PF00018 (Pfam clan CL0010), in InterPro at accession IPR001452; in SMART at accession SM00326; in PROSITE at accession PS50002; in the SCOP database at 1shf (Superfamily 1shf); and in CDD at accession cd00174. The SH3 domain is found in proteins that interact with other proteins and mediate assembly of specific protein complexes, typically via binding to proline-rich peptides in their respective binding partner (e.g., an SH3 ligand). In some embodiments, SH3 ligands comprise a consensus sequence that is:

P-X-X-P (SEQ ID NO: 9)

In some embodiments, each Pro is preceded by an aliphatic residue. In some embodiments, SH3 ligands comprise a consensus sequence that is:

—X—P-p-X—P— (SEQ ID NO: 10)

where the X at position 1 and 4 are aliphatic amino acids, the P at positions 2 and 5 are prolines, and the p at position 3 is sometimes a proline. The sequence binds to the hydrophobic pocket of the SH3 domain.

In some embodiments, SH3 domains bind to an SH3 ligand comprising a consensus sequence that is:

—R-x-x-K— (SEQ ID NO: 11)

where R is arginine, K is lysine, and x is any amino acid. Examples are the C-terminal SH3 domains of adaptor proteins like Grb2 and Mona (Gads, Grap2, Grf40, GrpL, etc.). See, e.g., Pawson and Schlessingert (1993) "SH2 and SH3 domains" Curr Biol. 3(7): 434-42, incorporated herein by reference. Saksela and Permi (2012) "SH3 domain ligand binding: What's the consensus and where's the specificity?" FEBS Letters 586: 2609-2614, incorporated herein by reference, provides several exemplary amino acid sequences of SH3 domains and identifies numerous SH3 ligands that find use in the present technology.

SH3 domains are often classified into two groups, e.g., Class 1 and Class 2, which recognize RKXXPXXP (SEQ ID NO: 12) and PXXPXR (SEQ ID NO: 13) motifs, respectively. Exemplary proteins comprising SH3 domains and SH3 ligand domains include, but are not limited to: Src tyrosine kinase and the p85 subunit of PI 3-kinase (comprising a RPLPVAP (SEQ ID NO: 14) Class I N-terminal to C-terminal binding site); Crk adaptor protein and C3G guanidine nucleotide exchanger (e.g., comprising a PPPALPPKKR (SEQ ID NO: 15) Class II C-terminal to N-terminal binding site); FYB (FYN binding protein) and SKAP55 Adaptor protein (e.g., comprising a RKGDYASY (SEQ ID NO: 16) binding site); Pexl3p (integral peroxisomal membrane protein) and Pex5p-PTS1 receptor (e.g., comprising a WXXQF (SEQ ID NO: 17) motif).

One of ordinary skill in the art is able to identify high-affinity SH3 domain-SH3 domain ligand binding partners. For example, combinatorial peptide libraries and phage display libraries find use in identifying high-affinity SH3 domain-SH3 domain ligand binding partners. These techniques have previously identified SH3 ligands, e.g., Class I peptides having an N-terminal Arg with the consensus sequence RXLPPZP (SEQ ID NO: 18) (Z represents Leu for the Src SH3 domain (Src SH3) and Arg for PI3K SH3) and Class II peptides having a C-terminal Arg with the consensus sequence XPPLPXR (SEQ ID NO: 19). Phage display libraries have indicated recognition motifs for the SH3 domains found in Src, Fyn, Lyn, Abl, and PI3K. The SH3 domains of Src, Fyn, Lyn, and PI3K bind a core recognition motif, RPLPPLP (SEQ ID NO: 20) and Abl SH3 binds the sequence PPPYPPPP(I/V)P (SEQ ID NO: 21).

3. PDZ Ligand/PDZ Domain Pairs

In some embodiments, a PDZ ligand and a PDZ domain provide one or more of the interacting orthogonal pairs of anchor subunits and dock subunits. A PDZ domain (also known as Dlg homologous region or GLGF (glycine-leucine-glycine-phenylalanine) (SEQ ID NO: 22)) comprises approximately 80-100 amino acids and is named for the first letters of three proteins that share the domain (post synaptic density protein (PSD95), *Drosophila* disc large tumor suppressor (Dlg1), and zonula occludens-1 protein (zo-1)). PDZ domains comprise 5 or 6 ß-stranded and 2 or 3 ⍵-helical structures and typically recognize the C-termini of target proteins, but some also recognize internal sequence motifs of PDZ ligands. PDZ domains bind to other specific proteins by beta sheet augmentation, e.g., the PDZ domain is extended by the addition of a further beta strand from the tail of the binding partner protein. Accordingly, one of ordinary skill in the art can identify PDZ domain-PDZ domain ligand pairs by analogy with known domains. See, e.g., Cowburn (1997) "Peptide recognition by PTB and PDZ domains" Curr Opin Struct Biol 7(6): 835-8, incorporated herein by reference. For example, combinatorial peptide libraries, phage display libraries, yeast two-hybrid, and co-immunoprecipitation find use in identifying high-affinity PDZ domain-PDZ domain ligand binding partners. Further, PDZ domain sequence accurately predicts binding specificity (see, e.g., Tonikian et al. (2008) "A specificity map for the PDZ domain family", PLoS Biol 6(9): e239, incorporated herein by reference). For instance, Tonikian provides 3,100 unique peptide ligands for 82 PDZ domains.

PDZ domains are found in many thousands of known proteins, including members of the domains eukaryotes, bacteria, archaea, and in viruses. In some embodiments, the technology comprises use of a PDZ domain from a well-studied human protein that comprises a PDZ domain, including, e.g., Erbin, GRIP, Htra1, Htra2, Htra3, PSD-95, SAP97, CARD11, and PTP-BL. In some embodiments, a PDZ domain finds use that is present in a protein that is, e.g., AAG12; AHNAK; AHNAK2; AIP1; ALP; APBA1; APBA2; APBA3; ARHGAP21; ARHGAP23; ARHGEF11; ARHGEF12; CASK; CLP-36; CNKSR2; CNKSR3; CRTAM; DFNB31; DLG1; DLG2; DLG3; DLG4; DLG5; DVL1; DVL1L1; DVL2; DVL3; ERBB2IP; FRMPD1; FRMPD2; FRMPD2L1; FRMPD3; FRMPD4; GIPC1; GIPC2; GIPC3; GOPC; GRASP; GRIP1; GRIP2; HTRA1; HTRA2; HTRA3; HTRA4; IL16; INADL; KIAA1849; LDB3; LIMK1; LIMK2; LIN7A; LIN7B; LIN7C; LMO7; LNX1; LNX2; LRRC7; MAGI1; MAGI2; MAGI3; MAGIX; MAST1; MAST2; MAST3; MAST4; MCSP; MLLT4; MPDZ; MPP1; MPP2; MPP3; MPP4; MPP5; MPP6; MPP7; MYO18A; NOS1; PARD3; PARD3B; PARD6A; PARD6B; PARD6G; PDLIM1; PDLIM2; PDLIM3; PDLIM4; PDLIM5; PDLIM7; PDZD11; PDZD2; PDZD3; PDZD4; PDZD5A; PDZD7; PDZD8; PDZK1; PDZRN3; PDZRN4; PICK1; PPP1R9A; 20 PPP1R9B; PREX1; PRX; PSCDBP; PTPN13; PTPN3; PTPN4; RAPGEF2; RAPGEF6; RGS12; RGS3; RHPN1; RIL; RIMS1; RIMS2; SCN5A; SCRIB; SDCBP; SDCBP2; SHANK1; SHANK2; SHANK3; SHROOM2; SHROOM3; SHROOM4; SIPA1; SIPA1L1; SIPA1L2; SIPA1L3; SLC9A3R1; SLC9A3R2; SNTA1; SNTB1; SNTB2; SNTG1; SNTG2; SNX27; SPAL2; STXBP4; SYNJ2BP; SYNPO2; SYNPO2L; TAX1BP3; TIAM1; TIAM2; TJP1; TJP2; TJP3; TRPC4; TRPC5; USH1C; or WHRN.

PDZ domains comprise a conserved motif:

R/K—XXX-G-$\Phi$-G-$\Phi$(SEQ ID NO: 23)

where X is any amino acid residue and $\Phi$ is a hydrophobic residue, e.g., in some embodiments located before the BB strand. The first Gly residue is variable and can be replaced by a Ser, Thr, or Phe residue in some embodiments. The second and the fourth residues are hydrophobic, such as Val, Ile, Leu, or Phe.

PDZ domain ligands comprise a beta-strand structure, e.g., at the C-terminus in some embodiments. In some embodiments, the PDZ domain ligand comprises, e.g., 4 to 10 residues.

In some embodiments, the PDZ domain and PDZ ligand are derived from a syntrophin (or PSD-95) protein and a nNOS protein.

In some embodiments, PDZ domains bind to ligands comprising the motif S/T-X-$\Phi$, or the motif $\Phi$-X-$\Phi$ or the motif D/E-X-$\Phi$, e.g., at the C-terminus of the PDZ ligand, where $\Phi$ represents a hydrophobic residue. In some embodiments, the PDZ ligand comprises a motif (e.g., a C-terminal motif) that is $\phi$-[K/R]—X—S-D-V (SEQ ID NO: 24); $\Omega$-[R/K]-E-T-[S/T/R/K]-$\phi$ (SEQ ID NO: 25); $\phi$-$\phi$-E-T-X-L (SEQ ID NO: 26); E-T-X-V (SEQ ID NO: 27); T-$\Psi$-T; $\Omega$-$\Omega$-T-W-$\Psi$ (SEQ ID NO: 28); $\phi$-$\phi$-$\phi$-[T/S]-[T/S]-$\Omega$-$\Psi$ (SEQ ID NO: 29); F-D-$\Omega$-$\Omega$-C(SEQ ID NO: 30); W—X-$\Omega$-D-$\Psi$ (SEQ ID NO: 31); W-$\Omega$-$\phi$-D-$\Psi$ (SEQ ID NO: 32); $\phi$-$\phi$-X-[E/D]-$\phi$-$\phi$-$\phi$ (SEQ ID NO: 33); $\phi$-$\phi$-$\phi$-$\phi$ (SEQ ID NO: 34); [D/E]-$\phi$-$\Omega$-$\phi$ (SEQ ID NO: 35); W-$\Omega$-[S/T]-D-W-$\Psi$ (SEQ ID NO: 36); $\Omega$-$\phi$-G-W—F (SEQ ID NO: 37), where $\phi$ indicates a hydrophobic amino acid (e.g., V, I, L, F, W, Y, M); $\Omega$ indicates an aromatic amino acid (e.g., F, W, Y); $\Psi$ indicates an aliphatic amino acid (e.g., V, I, L, and M); and X indicates any amino acid.

While these exemplary orthogonal binding pairs are described herein, the technology is not limited to these orthogonal binding pairs.

In some embodiments of the technology, each of the T cell-activating ligands (e.g., pMHC, CD80, and/or ICAM1) is each fused to a different anchor subunit (e.g., gene fusions are constructed to express fusion proteins comprising an N-terminal portion and a C-terminal portion, the N-terminal portion comprising the T cell-activating ligand (e.g., pMHC, CD80, or ICAM1) and the C-terminal portion comprising the anchor subunit); and, as described herein, each anchor subunit binds specifically to a unique dock subunit in the addressable protein scaffold. Further, in some embodiments, isolation of tumor-specific T cells from disease (e.g., cancer) patients and/or healthy donors is facilitated by using biotinylated pMHC complexes with no anchor subunit.

Moreover, because assembly of the supramolecular structure of the scaffold and bound T cell-activating components relies in some embodiments on the orthogonal high-affinity interactions between dock subunits and anchor subunits, embodiments of the technology comprise a sequential assembly process to provide correct pattern formation. For example, in some embodiments, the display (e.g., expression, arrangement, assembly) of the one or more primary anchor proteins (e.g., on the cell surface, solid support, or in soluble form) is first confirmed using flow cytometry. Then, in some embodiments, the correct binding of the dock proteins (e.g., each comprising one or more dock subunits) onto the one or more primary anchor proteins is confirmed, e.g., using flow cytometry and/or stimulated emission depletion (STED) microscopy. Finally, in some embodiments, the T cell-activating ligands (pMHC, CD80, and ICAM1) fused to anchor subunits are loaded onto the addressable protein scaffold separately (e.g., one at a time in a prescribed order) and in some embodiments the T cell-activating ligands (pMHC, CD80, and ICAM1) fused to anchor subunits are loaded onto the addressable protein scaffold in combination (e.g., in combinations of two (e.g., pMHC and CD80; CD80 and ICAM1; pMHC and ICAM1) or all three at once). In some embodiments, the displayed proteins are evaluated using confirmation-sensitive antibodies and/or STED microscopy.

The technology provided herein (e.g., tunable and scalable protein assemblies (TSPAs) and associated methods and systems) find use as a high-throughput engineering technology platform for the design and development of effective and affordable personalized immunotherapy, and as a high-throughput screening tool to evaluate signals for T cell activation and/or expansion, e.g., as a research tool to advance the understanding of the molecular mechanisms of antigen presentation and recognition by T cells.

Embodiments of the technology relate to the design and synthesis of the TSPA components and, in some embodiments, their assembly into an artificial immunological synapse with a defined pattern (e.g., in some embodiments, a bull's eye pattern). Accordingly, the technology provides, in some embodiments, an artificial APC (aAPC) system that elicits sustained and potent antigen-specific (e.g., tumor-specific) T cell responses in vivo and/or ex vivo, thus providing, in some embodiments, an immunotherapy to treat many different types of diseases (e.g., cancer, infectious disease, and other immune-modulating diseases).

Data have indicated that T cell activation and the functional outcome of activation depend not only on the recognition of the antigen (e.g., tumor antigen), but also on the context in which the antigen is presented by the APC and subsequently recognized by the T cell (e.g., by the T cell receptor). This contextual milieu at the APC-T cell interface is termed the immunological synapse (IS; see, e.g., FIG. 1A). Cytokine signals further modulate the specificity, activation, and function of the T cell upon activation by the IS. A productive IS formation involves an array of receptor-ligand interactions that dynamically organize into a supramolecular structure. While present technologies use only homogeneous antigen presentation to T cells, the technologies described herein use patterned signal presentation (e.g., using a TSPA) for improved activation and expansion of antigen-specific (e.g., tumor-specific) T cells.

Accordingly, embodiments of the technology relate to the design and synthesis of the components of the TSPA described herein, e.g., components of the addressable protein scaffold (e.g., comprising one or more primary anchor proteins and one or more dock proteins) and the T cell activating ligands (e.g., pMHC, CD80, and ICAM1) each fused to an anchor subunit that assemble on the addressable protein scaffold to provide the patterned immunological synapse and subsequently provide improved T-cell activation.

The TSPA comprises orthogonal pairs of dock and anchor subunits that specifically interact, e.g., with a high affinity ($K_d \sim 10^{-9}$ to $10^{-12}$ M or stronger), to direct the assembly of the T cell activating proteins into a supramolecular IS-mimicking pattern (see, e.g., FIG. 1). In some embodiments, the orthogonal pairs of dock subunits and anchor subunits are based on high-affinity ligand-receptor interactions, e.g., scFv antibodies, signaling receptors, and cohesins. In some embodiments, the technology comprises nucleic acids (e.g., cloned into a suitable vector to provide for the manipulation of the nucleic acids) that express dock proteins (comprising one or more dock subunits), primary anchor proteins (comprising one or more anchor subunits), and/or T cell activating ligands fused to anchor proteins. For example, in some embodiments the dock subunit-anchor subunit pairs are cloned from murine spleenocytes and microbial strains (e.g., *C. thermocellum, C. cellulolyticum, C. cellulovorans,* and *R. flavefaciens*).

In some embodiments, the T cell activating pattern is produced using the TSPA technology provided herein, in particular using one or more primary anchor proteins, one or more dock proteins, and one or more T cell activating ligands. Assembly of the TSPA is mediated by interactions between 1) anchor subunits of the primary anchor protein and dock subunits of the dock proteins; and 2) anchor subunits fused to the T cell activating ligands and dock subunits of the dock proteins. The technology uses one or more pairs (e.g., 1, 2, 3, 4, 5, 6, 7, 8, 9, or 10 or more pairs) of interacting orthogonal pairs of dock subunits and anchor subunits to provide the specific interactions that guide the assembly (e.g., self-assembly) of the TSPA.

In an exemplary embodiment (see, e.g., FIG. 1) to illustrate the technology, 6 dock subunit-anchor subunit pairs are used. As used herein, distinct anchor subunits are identified using the letter "a" followed by an identifier (e.g., a number, a number and a letter, etc.) to distinguish different anchor subunits from each other, e.g., a1, a2, a3, a4, a5, and a6; aA1, aB1, aC1, aD1. As used herein, distinct dock subunits are named using the letter "d" followed by an identifier (e.g., a number, a number and a letter) to distinguish different dock subunits from each other, e.g., d1, d2, d3, d4, d5, and d6; dA1, dB1, dC1, dD1. Further, each dock subunit identified by the identifier n ("dn") binds to the corresponding anchor subunit having the same identifier n ("an") as the dock subunit.

According to this terminology, a1 binds d1, but a1 does not bind any of the other dock subunits d2, d3, d4, d5, or d6; a2 binds d2, but a2 does not bind any of the other dock subunits d1, d3, d4, d5, or d6; a3 binds d3, but a3 does not bind any of the other dock subunits d1, d2, d4, d5, or d6; a4 binds d4, but a4 does not bind any of the other dock subunits d1, d2, d3, d5, or d6; a5 binds d5, but a5 does not bind any of the other dock subunits d1, d2, d3, d4, or d6; and a6 binds d6, but a6 does not bind any of the other dock subunits d1, d2, d3, d4, or d5. Similarly, according to this terminology, d1 binds a1, but d1 does not bind any of the other anchor subunits a2, a3, a4, a5, or a6; d2 binds a2, but d2 does not bind any of the other anchor subunits a1, a3, a4, a5, or a6; d3 binds a3, but d3 does not bind any of the other anchor subunits a1, a2, a4, a5, or a6; d4 binds a4, but d4 does not bind any of the other anchor subunits a1, a2, a3, a5, or a6; d5 binds a5, but d5 does not bind any of the other anchor subunits a1, a2, a3, a4, or a6; and d6 binds a6, but d6 does not bind any of the other anchor subunits a1, a2, a3, a4, or a5.

Embodiments provide construction of the protein scaffold from one or more (e.g., 1, 2, 3, 4, 5, 6, 7, 8, 9, 10, or more) primary anchor proteins. Each primary anchor protein comprises one or more (e.g., 1, 2, 3, 4, 5, 6, 7, 8, 9, 10, or more) anchor subunits. For example, in some embodiments, a recombinant nucleic acid is provided that encodes a primary anchor protein. The recombinant nucleic acid encoding the primary anchor protein encodes one or more (e.g., 1, 2, 3, 4, 5, 6, 7, 8, 9, 10, or more) anchor subunits, e.g., as a fusion protein comprising one or more (e.g., 1, 2, 3, 4, 5, 6, 7, 8, 9, 10, or more) anchor subunits linked together (e.g., linked together serially). In some embodiments, the recombinant nucleic acid encoding a primary anchor protein comprises a nucleotide sequence comprising the coding sequences for one or more (e.g., 1, 2, 3, 4, 5, 6, 7, 8, 9, 10, or more) anchor subunits linked together. In some embodiments, the primary anchor protein comprising one or more (e.g., 1, 2, 3, 4, 5, 6, 7, 8, 9, 10, or more) anchor subunits linked together comprises one or more (e.g., 1, 2, 3, 4, 5, 6, 7, 8, 9, 10, or more) linkers (e.g., one or more (e.g., 1, 2, 3, 4, 5, 6, 7, 8, 9, 10, or more) linker peptides) between anchor subunits. In some embodiments, the recombinant nucleic acid comprises a nucleotide sequence comprising the coding sequences for one or more (e.g., 1, 2, 3, 4, 5, 6, 7, 8, 9, 10, or more) anchor subunits linked together and the coding sequences for one or more (e.g., 1, 2, 3, 4, 5, 6, 7, 8, 9, 10, or more) linkers (e.g., one or more (e.g., 1, 2, 3, 4, 5, 6, 7, 8, 9, 10, or more) linker peptides) between anchor subunits. In some embodiments, a primary anchor protein is produced by producing a first polypeptide comprising one or more (e.g., 1, 2, 3, 4, 5, 6, 7, 8, 9, 10, or more) anchor subunits (e.g., by expression of a first nucleic acid encoding the one or more (e.g., 1, 2, 3, 4, 5, 6, 7, 8, 9, 10, or more) anchor subunits) and linking (e.g., chemically linking) the first polypeptide to a second polypeptide comprising one or more (e.g., 1, 2, 3, 4, 5, 6, 7, 8, 9, 10, or more) additional anchor subunits (e.g., produced by expression of a second nucleic acid encoding the one or more (e.g., 1, 2, 3, 4, 5, 6, 7, 8, 9, 10, or more) additional anchor subunits). In some embodiments, a primary anchor protein comprising one or more (e.g., 1, 2, 3, 4, 5, 6, 7, 8, 9, 10, or more) anchor subunits is produced by direct chemical peptide synthesis. Nucleic acids encoding one or more (e.g., 1, 2, 3, 4, 5, 6, 7, 8, 9, 10, or more) anchor subunits are produced according to technologies known in the art, e.g., by direct synthesis, restriction and ligation, polymerase chain reaction, and other nucleic acid cloning and manipulation techniques.

In some embodiments, a primary anchor protein is linked to a protein that is expressed on the surface of a cell. Accordingly, in some embodiments, one or more (e.g., 1, 2, 3, 4, 5, 6, 7, 8, 9, 10, or more) anchor subunits is linked to a protein that is expressed on the surface of a cell. In some embodiments, a primary anchor protein comprises one or more (e.g., 1, 2, 3, 4, 5, 6, 7, 8, 9, 10, or more) anchor subunits, a protein that is expressed on the surface of a cell (e.g., a yeast cell), and, in some embodiments, one or more (e.g., 1, 2, 3, 4, 5, 6, 7, 8, 9, 10, or more) linkers between one or more (e.g., 1, 2, 3, 4, 5, 6, 7, 8, 9, 10, or more) anchor subunits and/or between an anchor subunit and the protein that is expressed on the surface of a cell. In some embodiments, the protein that is expressed on the surface of a cell is a protein that finds use in yeast display (e.g., yeast surface display), e.g., a protein that is expressed on the surface of a yeast cell, e.g., a protein known in the art as Aga2p. Yeast display is a technique in which a protein of interest (e.g., a primary anchor protein comprising one or more (e.g., 1, 2, 3, 4, 5, 6, 7, 8, 9, 10, or more) anchor subunits; an anchor subunit) is displayed as a fusion to the Aga2p protein on the surface of yeast. The Aga2p protein is naturally used by yeast to mediate cell-cell contacts during yeast cell mating. As such, display of a protein via Aga2p projects the protein away from the cell surface. See, e.g., Boder and Wittrup (1997) "Yeast surface display for screening combinatorial polypeptide libraries" Nat. Biotech. 15: 553-57, incorporated herein by reference. The gene encoding Aga2p is AGA2. Aga2p is the adhesion subunit of a-agglutinin expressed by a-cells; the C-terminal sequence is a ligand for alpha-agglutinin (Sagip) during agglutination. Aga2' is modified with O-linked oligomannosyl chains and linked to Agalp via two disulfide bonds.

Accordingly, as an exemplary illustration of the technology (e.g., as shown in FIG. 1), a primary anchor protein is produced comprising a plurality of anchor subunits, e.g., a3-a2-a1-a1-a2-a3, linked to the Aga2p protein for yeast surface display. As used herein, a primary anchor protein is a protein comprising one or more (e.g., 1, 2, 3, 4, 5, 6, 7, 8, 9, 10, or more) anchor subunits and, in some embodiments, a protein for cell surface display (e.g., yeast display, e.g., Aga2p).

After surface display of the one or more primary anchor proteins (e.g., comprising one or more (e.g., 1, 2, 3, 4, 5, 6, 7, 8, 9, 10, or more) anchor subunits and, in some embodiments, a protein for cell surface display (e.g., yeast display, e.g., Aga2p)), one or more (e.g., 1, 2, 3, 4, 5, 6, 7, 8, 9, 10, or more) soluble dock proteins (e.g., each comprising one or more (e.g., 1, 2, 3, 4, 5, 6, 7, 8, 9, 10, or more) dock subunits) are provided for interaction with the primary anchor proteins.

As an exemplary illustration of the technology (e.g., as shown in FIG. 1), three soluble dock proteins (D1, D2, and D3) are provided, e.g.:

D1: d4-d5-d6-d5-d4-d1;
D2: d4-d5-d5-d5-d4-d2; and
D3: d4-d4-d4-d4-d4-d3.

In this exemplary embodiment, the three dock proteins D1, D2, and D3 assemble onto the primary anchor protein to produce the protein scaffold. The d1 of the first dock protein D1 interacts with the a1 of the primary anchor protein; the d2 of the second dock protein D2 interacts with the a2 of the primary anchor protein; and the d3 of the third dock protein D3 interacts with the a3 of the primary anchor protein. The protein scaffold comprises dock subunits in a pattern with which the T cell activating ligands interact to form the TSPA (e.g., to form the IS) pattern (e.g., in some embodiments, a bull's eye pattern).

In some embodiments, a primary anchor protein and/or a dock protein comprises a protein tag to provide for the detection and/or visualization of the addressable protein scaffold assembly (e.g., using flow cytometry, STED microscopy, etc.). In some embodiments, the protein tag is a V5 epitope tag (e.g., comprising the amino acid sequence GKPIPNPLLGLDST, SEQ ID NO: 1), a c-myc tag (e.g., comprising the amino acid sequence EQKLISEEDL, SEQ ID NO: 2), a HA tag (e.g., comprising the amino acid sequence YPYDVPDYA, SEQ ID NO: 3), an affinity tag, a fluorescent tag, or other tags known in the art. For example, in some embodiments the primary anchor protein comprises a C-terminal V5 epitope tag and/or the dock protein comprises a C-terminal c-myc tag to provide for the detection and visualization of the addressable protein scaffold assembly using flow cytometry and/or STED microscopy. Epitope tags are recognized by antibodies specific for the epitope, e.g., for detection, visualization, isolation, etc.

Embodiments of the technology provide an artificial antigen presenting system that comprises functional peptide-MHC (pMHC) complexes (e.g., on a cell surface, on a solid support, on a bead, etc.) to engage a T cell, e.g., to interact with a T-cell receptor, e.g., to form an IS or IS-like structure. Further, the interaction of the pMHC complexes with the T-cell receptor determines the specificity of the T-cell activation. Accordingly, in some embodiments, the pMHC protein is fused to an anchor subunit that directs its docking to a dock subunit at the appropriate location within the IS pattern provided by the protein scaffold. For example, for a bull's eye pattern, the pMHC protein is fused to an anchor subunit that directs its docking onto the center of the addressable protein scaffold. In additional embodiments, the CD80 and ICAM1 are fused to a second and a third anchor subunit to direct their assembly in concentric rings around the pMHC (see, e.g., FIG. 1).

pMHC Proteins

In some embodiments, the technology comprises the detecting and/or isolating antigen-specific T cells, e.g., from healthy donors. Accordingly, in some embodiments, the pMHC protein is biotinylated, e.g., in some embodiments, expressed without being fused to an anchor subunit and comprising a biotinyl group. In some embodiments, the pMHC complexes are in a tetrameric form, which provide for the detection and/or isolation of antigen-specific T cells from healthy donors. Therefore, in some embodiments the technology provides a system for producing multiple forms of class I pMHC (pMHCI) and class II (pMHCII) complexes. Some embodiments comprise a pMHC comprising an MHC encoded by a prevalent MHC allele, e.g., A*0201, B*0702, DR*0101, DR*0401, DR*0701, and DR*1501) to provide coverage of approximately 50% of the Caucasian population. Accordingly, this technology finds use in personalized cancer immunotherapy.

Some embodiments provide a biotinylated MHC (e.g., a biotinylated MHCI, a biotinylated MHCII). For example, in some embodiments, a biotinylated MHC comprises a conditionally cleavable ligand design that provides for the rapid exchange of numerous (e.g., hundreds, thousands, tens of thousands, hundreds of thousands, millions) peptides.

For example, in some embodiments of the technology provided herein, MHCI alleles are expressed in an expression system, e.g., as inclusion bodies in E. coli. In some embodiments, the expressed MHCI proteins are refolded in the presence of a peptide, e.g., a cleavable (e.g., an ultraviolet-light cleavable) peptide. For example, in exemplary experiments, an MHCI allele is refolded in the presence of a peptide comprising an amino sequence GILGFVFJL (SEQ ID NO: 4) to produce an MHCI-GILGFVFJL peptide and, in some embodiments, an allele is refolded in the presence of a peptide comprising an amino sequence AARGJTLAM (SEQ ID NO: 5) to produce an MHCI-AARGJTLAM peptide. See, e.g., Example 1. See also Example 11.

Experimental data validated peptide exchange of the MHCI-peptide fusions with several peptides (e.g., viral peptides, antigenic peptides). Exchange does not depend on the source of the peptides; accordingly, other peptides (e.g., antigen peptides, tumor-associated peptides) are contemplated also to undergo exchange in this system. In some embodiments, MHC tetramers are prepared, e.g., using a streptavidin-dye conjugate (e.g., streptavidin-phycoerythrin) to stain CD8+ T cells. In some embodiments, CD8+ cells are isolated from a healthy donor. See, e.g., Example 1.

Figure 3:
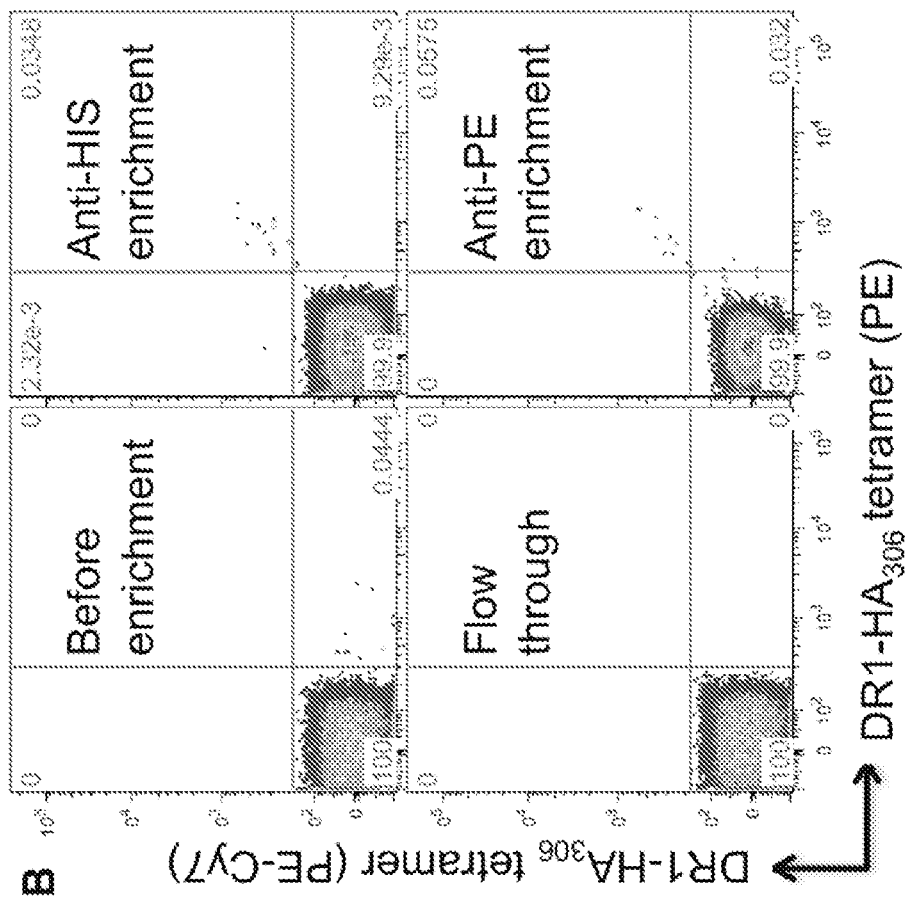
FIG. 3A shows a schematics of a CLIP-MHCII construct described herein and, in some embodiments, expressed in insect cells. The zipper and CLIP peptide stabilize the heterodimeric MHCII, the BirA tag allows biotinylation, and the HIS tag allows rapid purification using nickel resin. The anchor a6 subunit is only included when the pMHCII complex is immobilized on the aAPC.
FIG. 3B shows flow cytometry data of DR1-HA306 tetramer staining of CD4+ T cells isolated from a healthy DR1+ donor. The DR1-HA306 complex was generated by peptide exchange after enzymatic cleavage of the CLIP peptide and tetramerized using both streptavidin conjugate to PE or PE-Cy7. The rare DR1-HA306-318-specific T cells (~1-2 in one million CD4+ T cells) were enriched using either anti-HIS or anti-PE magnetic beads with comparable efficiencies.
Figure 3:
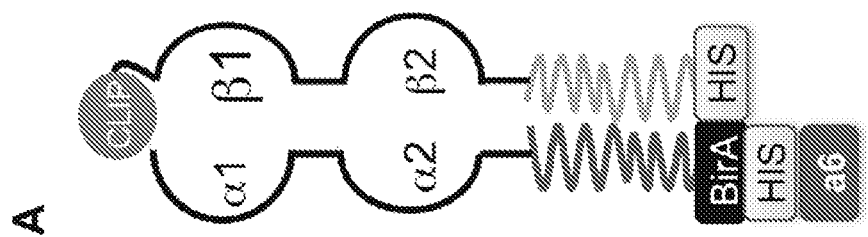

Some embodiments relate to preparing class II MHC, class II pMHC, and class II pMHC tetramers. In some embodiments, peptide exchange is used to prepare class II pMHC. For instance, some embodiments comprise use of a peptide-exchangeable construct (e.g., in an expression system, e.g., in Chinese hamster ovary cells) in which a class II-associated invariant chain peptide ("CLIP peptide") is fused to the N-terminus of the MHCII beta subunit (e.g., an MHCII beta subunit allele such as a HLA-DR6 chain), e.g., by a cleavable linker, e.g., comprising a thrombin cleavage site (see, e.g., FIG. 6). Related embodiments comprise use of the CLIP-MHCII6 design and an expression system, e.g., in insect cells, to provide an efficient and simple protein expression and purification system (see, e.g., FIG. 3A). MHCII is an αs heterodimer, cell surface receptor, each subunit of which contains two extracellular domains, a membrane-spanning domain, and a cytoplasmic tail. Both a and 6 chains are anchored in the membrane. The N-terminal domain of the mature protein forms an alpha-helix that constitutes the exposed part of the binding groove, the C-terminal cytoplasmic region interact with the other chain forming a beta-sheet under the binding groove spanning to the cell membrane. The majority of the peptide contact positions are in the first 80 residues of each chain. The complex of MHCII and its ligand, a peptide (e.g., of approximately 9 amino acids in length or longer), provides a ligand for the T-cell receptor (TCR). See, e.g., Example 2.

Some embodiments comprise (and comprise the use of) complexes of CLIP and MHCII (e.g., MHCIIB) that are produced and/or purified. In some embodiments, CLIP-MHCII (e.g., CLIP-MHCIIB) complexes provide a peptide-exchangeable construct that finds use to form functional tetramers with desired TCR-binding specificities (see, e.g., FIG. 3B). Furthermore, some embodiments of the technology comprise use of an enrichment protocol, e.g., using anti-HIS magnetic beads or other enrichment methods known in the art, to provide for the isolation and enrichment of specific (e.g., tumor-specific) CD4+ T cells from patients (e.g., cancer patients) and their characterization, e.g., using metal-tagged antibodies via mass cytometry. Embodiments further relate to cloning, expressing, and purifying CLIP-MHCII allele complexes. See, e.g., Example 2.

The pMHC complexes described herein (e.g., pMHCI and pMHCII) find use in antigen-specific (e.g., tumor-specific) T-cell detection and isolation from healthy donors or disease (e.g., cancer) patients. In some embodiments, the pMHC complexes are immobilized on the addressable protein scaffold by fusion of an anchor subunit (e.g., a6) to the pMHC. In some embodiments relating to pMHCII, the anchor subunit (e.g., a6) is fused to the C-terminus of the MHCII DRa chain after the HIS tag (see, e.g., FIG. 3A). In experiments conducted during the development of the technologies described herein, CLIP-DR1-a6 was successfully expressed and purified. Furthermore, in some embodiments HA-DR1-a6 is produced by peptide exchange with the CLIP-DR1-a6 fusion protein. In some embodiments, the IL-2 response of a T cell hybridoma expressing TCR specific for HA-DR1 is used to test embodiments of the constructs described herein, e.g., for full activation, not only early stage activation, of T cells. Embodiments further comprise other pMHCII-anchor subunit fusion proteins. Further embodiments comprise fusion proteins comprising an anchor subunit (e.g., a6) and pMHCI (e.g., a protein comprising an anchor subunit fused and/or linked to the C-terminus of the 62 chain pMHCI).

Immunological Synapse Proteins

The technology relates to activating T cells by contacting T cells with a pMHC complex in an arrangement that mimics an immunological synapse. Accordingly, the technology relates to the use of proteins in addition to pMHC that are involved in T-cell activation, e.g., the costimulatory protein CD80 and the adhesion protein ICAM1. Accordingly, in some embodiments TSPA find use to co-present CD80 and/or ICAM1 with pMHC. For instance, the technology provides polypeptide constructs in which the extracellular domain of CD80 and/or ICAM1 is fused to an anchor subunit (e.g., a5, a4) and, in some embodiments, a HIS tag. In some embodiments, the CD80 and/or ICAM1 constructs (e.g., comprising an anchor subunit) are expressed in an expression system, e.g., an in vitro expression system, e.g., a eukaryotic expression system, e.g., expressed in an insect cell system, e.g., expressed in High Five insect cells, and purified using nickel-affinity and/or size-exclusion chromatography. Further, the function of the expressed recombinant proteins is tested, e.g., by staining human T cells isolated from human blood using fluorescent anti-HIS antibody as a secondary antibody. The signals are compared to staining with antibodies specific for proteins that bind to CD80 and ICAM21, e.g., anti-CD28 and anti-LFA3 staining (CD80 binds CD28 and ICAM1 binds LFA3).

During the development of the technology provided herein, the genes encoding CD80 and ICAM1 were cloned using mRNA isolated from human peripheral blood mononuclear cells as the template. The genes are expressed to provide the CD80 and ICAM1 proteins for use in the technology described herein.

Assembly of the Immunological Synapse Pattern

The protein components described herein find use in the assembly of the immunological synapse pattern according to the orthogonal high-affinity interaction between the dock and anchor subunits. Experiments are conducted to confirm the display of the primary anchor protein on the cellular surface (e.g., yeast cell surface) by staining for the V5 signal, which indicates full-length protein expression. Then, each of the purified dock proteins is added, e.g., separately and in combination, to verify assembly of the addressable protein scaffold by measuring anti-V5 and anti-c-myc signal(s) using flow cytometry. Additionally, stimulated emission depletion (STED) microscopy is used to visualize the supramolecular structure. Finally, the pMHC-anchor subunit (e.g., a6), CD80-anchor subunit (e.g., a5), and ICAM1-archor subunit (e.g., a4) are loaded onto the protein scaffold, e.g., separately and in combination. Flow cytometry and antibody staining are used to stain pMHCII, pMHCI, CD80, and ICAM1. In some embodiments, the antibodies L243, BB7.2, L307.4, and 3E2 are used to stain pMHCII, pMHCI, CD80, and ICAM1, respectively. Observing a triple-positive population of cells indicates correct assembly of the TSPA structure, e.g., that the dock-anchor interaction has directed the assembly of an IS-mimicking pattern on the aAPC surface. Assembly is further confirmed using STED microscopy. Further, experiments conducted during the development of embodiments of the technology validated that pMHC-anchor fusion protein are immobilized to the scaffold protein (see, e.g., Example 3). In some embodiments, HA-DR1-a6 is produced by peptide exchange and to activate T cells (e.g., a T cell hybridoma).

Figure 4:
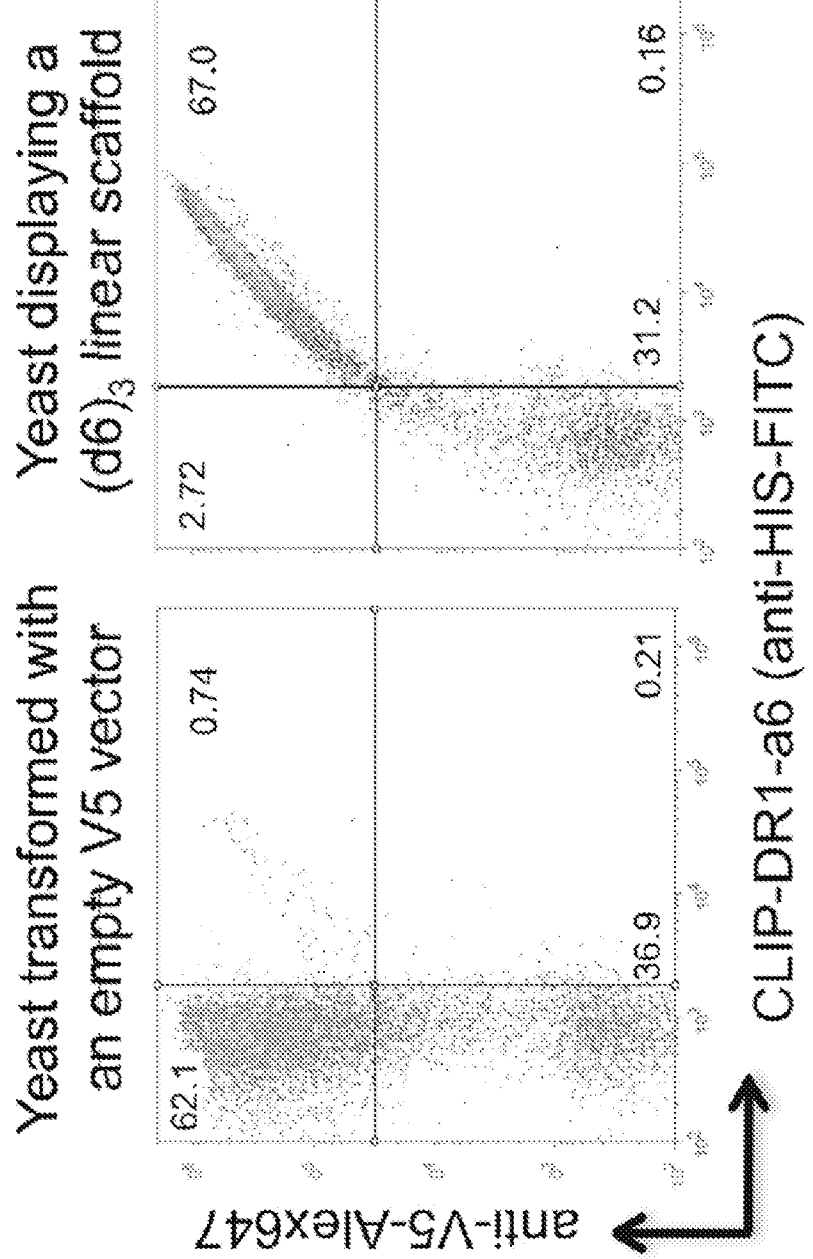
FIG. 4 shows flow cytometry data indicating assembly of a pMHC protein on a scaffold. Purified CLIP-DR1-a6 protein was loaded onto yeast cells expressing an empty V5 vector or a V5 vector with a scaffold insert $(d6)_3$. The CLIP-DR1-a6 is anchored on the surface in a scaffold-dependent manner.

The data collected in experiments conducted during the development of embodiments of the technology indicate that the pMHC-anchor fusion protein is immobilized on a protein scaffold containing the binding dock subunits (FIG. 4). Although in these particular experiments, a scaffold protein was expressed in yeast that is different from the addressable scaffold protein as described herein, the shared mechanism for pMHC anchorage indicates that the assembly technology described herein provides the assembled pattern, e.g., of an IS. In some experiments examining the assembled scaffold, tris (2-carboxyethyl) phosphine is used to detach the primary scaffold from the yeast cell for direct visualization of the supramolecular structure.

Activation of T Cells

The technology relates to isolating T cells and activating T cells (e.g., tumor-specific T cells) with the TSPA technology. Furthermore, the technology finds use in investigating the relationship between TSPA configuration and induced T-cell phenotype and function. In some embodiments, the supramolecular organization of the T-cell-activating ligands is different for different types of T cell interactions. Accordingly, the technology comprises the formation of a variety of immunological synapse patterns. In some embodiments, the IS comprises a bulls-eye pattern. However, the technology is not limited to IS patterns having a bulls-eye shape. Indeed, the technology finds use in activating T cells with any pattern, e.g., bulls-eye synapses, multifocal synapses, polarized synapses, and dynamic synapses/kinapses. See, e.g., Thauland and Parker (2010) "Diversity in immunological synapse structure" *Immunology* 131: 466-472; Alarcon et al. (2011) "The immunological synapse: a cause or consequence of T-cell receptor triggering?" *Immunology* 133: 420-425, each incorporated herein by reference.

Accordingly, embodiments of the technology relate to TSPA with a variety of T-cell-activating ligands in a variety of patterns. In some embodiments, TSPAs comprise the proteins pMHC, CD80, and ICAM1 and in some embodiments the TSPAs comprise the proteins pMHC, CD137L, and ICAM1). In some embodiments, the proteins are arranged in a bulls-eye pattern and in some embodiments the proteins are arranged homogeneously. The TSPAs find use in expanding T cells (e.g., tumor-specific T cells). In some embodiments, data are collected (e.g., high dimensional data) and analyzed to reveal correlations between TSPA composition, ligand-presentation pattern, and the anti-tumor function of the expanded T cells to provide information on which to provide a cancer immunotherapy. Experiments conducted to test the isolation and activation of antigen-specific T cells (e.g., tumor-specific T cells) are described in Example 4.

Pharmaceutical Formulations

It is generally contemplated that activated T cells produced by contacting T cells with a pMHC (e.g., as presented in an IS-like pattern using a TSPA) related to the technology are formulated for administration to a mammal, and especially to a human with a condition (e.g., cancer, infection, etc.) that is responsive to the administration of such compositions. Therefore, where T cells are administered in a pharmacological composition, it is contemplated that the T cells are formulated in admixture with a pharmaceutically acceptable carrier. For example, T cells can be administered intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. It is also well within the ordinary skill of the art to modify the route of administration and dosage regimen of a particular composition to manage the pharmacokinetics for maximum beneficial effect in a patient.

With respect to administration to a subject, it is contemplated that the T cells be administered in a pharmaceutically effective amount. One of ordinary skill recognizes that a pharmaceutically effective amount varies depending on the the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise activated T cells produced according to the technology provided herein associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro ed., 1985), explicitly incorporated herein by reference for all purposes.

Accordingly, in some embodiments, the immunotherapeutic agent is formulated as a sterile solution, e.g., a sterile solution prepared for use as an infusion.

The technology also provides methods for preparing stable pharmaceutical preparations containing aqueous suspensions or solutions of the T cells to inhibit formation of degradation products. A solution is provided that contains the T cells and at least one inhibiting agent. The solution is processed under at least one sterilization technique prior to and/or after filling a container to form a stable pharmaceutical preparation.

In some embodiments, the compositions comprising T cells are formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the compositions comprising T cells are formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the compositions comprising T cells are formulated formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compositions are formulated formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the compositions comprising T cells are formulated formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation comprising T cells may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

Administration, Treatments, and Dosing

In some embodiments, the technology relates to methods of providing a dosage of a activated T cells to a subject. In some embodiments, the methods comprise administering T cells produced according to the technology, measuring a level of a biomarker in a sample obtained from the subject, and adjusting the dose based on the measured level of the biomarker.

In some embodiments, T cells are administered in a pharmaceutically effective amount. In some embodiments, T cells are administered in a therapeutically effective dose.

The dosage amount and frequency are selected to create an effective level of the T cells within the subject without substantially harmful effects. When administered, the dosage of the T cells will generally range from $10^6$ to $10^{10}$ T cells. For example, in some embodiments the dosage is $10^9$ to $10^{10}$ T cells/m$^2$ of patient body surface area (e.g., for ex vivo expanded T cells) and for cells comprising artificial T cell receptors (e.g., CAR-T cells) the dosage is from $10^6$ to $10^7$ cells/kg of patient body weight.

Methods of administering a pharmaceutically effective amount include, without limitation, administration in parenteral routes, for example, subcutaneous, intravenous, intramuscular, intrastemal injection, and infusion routes.

In some embodiments, a single dose of T cells is administered to a subject. In other embodiments, multiple doses are administered over two or more time points, separated by hours, days, weeks, etc. In some embodiments, T cills are administered over a long period of time (e.g., chronically), for example, for a period of months or years (e.g., 1, 2, 3, 4, 5, 6, 7, 8, 9, 10, 11, 12, or more months or years). In such embodiments, T cells may be administered on a regular scheduled basis (e.g., daily, weekly, etc.) for the duration of the extended period.

The technology also relates to methods of treating a subject with T cells, e.g., T cells activated according to the technology provided herein. In some embodiments, a method is provided for treating a subject in need of such treatment with an effective amount of T cells, e.g., T cells isolated from the subject and activated by contacting the T cells with a pMHC (e.g., a pMHCI, a pMHCII) presented in an IS-like pattern by a scaffold. The method involves administering to the subject an effective amount of T cells in any one of the pharmaceutical preparations described above, detailed herein, and/or set forth in the claims. The subject can be any subject in need of such treatment.

In some embodiments, a subject is tested to assess the presence, the absence, or the level of a malady and/or a condition. Such testing is performed, e.g., by assaying or measuring a biomarker, a metabolite, a physical symptom, an indication, etc., to determine the risk of or the presence of the malady or condition. In some embodiments, the subject is treated with T cells based on the outcome of the test. In some embodiments, a subject is treated, a sample is obtained and the level of detectable agent is measured, and then the subject is treated again based on the level of detectable agent that was measured. In some embodiments, a subject is treated, a sample is obtained and the level of detectable agent is measured, the subject is treated again based on the level of detectable agent that was measured, and then another sample is obtained and the level of detectable agent is measured. In some embodiments, other tests (e.g., not based on measuring the level of detectable agent) are also used at various stages, e.g., before the initial treatment as a guide for the initial dose. In some embodiments, a subsequent treatment is adjusted based on a test result, e.g., the dosage amount, dosage schedule, identity of a co-administered drug, etc. is changed. In some embodiments, a patient is tested, treated, and then tested again to monitor the response to therapy and/or to change the therapy. In some embodiments, cycles of testing and treatment occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/test/treat, test/treat/test/treat/test, treat/test/test/test/treat/treat/test, treat/treat/test/treat, test/treat/treat/test/treat/treat, etc.

Kits

Some embodiments provide kits for activation of T cells and/or for provision of a therapeutic composition comprising activated T cells. For example, some embodiments provide a TSPA in assembled form, e.g., assembled on a cell (e.g., a yeast cell) or assembled on a solid support (e.g., a bead), that finds use in activating T cells. Some embodiments provide a TSPA in a disassembled form, e.g., for assembly by a user. In some embodiments, the TSPA comprises an MHC (e.g., MHCI or MHCII) comprising a peptide that is exchanged with an antigenic peptide appropriate for the subject to be treated (e.g., a peptide comprising an antigen appropriate for producing activated T cells that will treat the subject's disease). Some embodiments of kits further comprise one or more cytokines for activation of T cells. Embodiments of kits comprise pharmaceutical formulations for suspending T cells to provide a formulation for administration to a subject. Some embodiments provide culture medium for the growth and expansion of activated T cells prior to administration to a subject. Some embodiments of kits comprise anti-HIS beads (e.g., magnetic beads) or other enrichment methods to provide for the isolation and enrichment of specific (e.g., tumor-specific) T cells from patients.

Although the disclosure herein refers to certain illustrated embodiments, it is to be understood that these embodiments are presented by way of example and not by way of limitation.

EXAMPLES

Example 1—Production of MHCI Proteins

During the development of embodiments of the technology provided herein, a plurality of MHCI alleles were expressed (e.g., A2 (e.g., A*0201) and B7 (B*0702)) as inclusion bodies in *E. coli* and refolded in the presence of a cleavable (e.g., an ultraviolet-light cleavable) peptide. For example, in exemplary experiments, the first allele was refolded in the presence of a peptide comprising an amino sequence GILGFVFJL (SEQ ID NO: 4) to produce an A2-GILGFVFJL peptide and the second allele was refolded in the presence of a peptide comprising an amino sequence AARGJTLAM (SEQ ID NO: 5) to produce a B7-AARGJTLAM peptide.

Experimental data validated peptide exchange of the A2-GILGFVFJL protein with several peptides (e.g., viral peptides). Exchange does not depend on the source of the peptides; accordingly, other peptides (e.g., tumor-associated peptides) are contemplated also to undergo exchange in this system.

Figure 2:
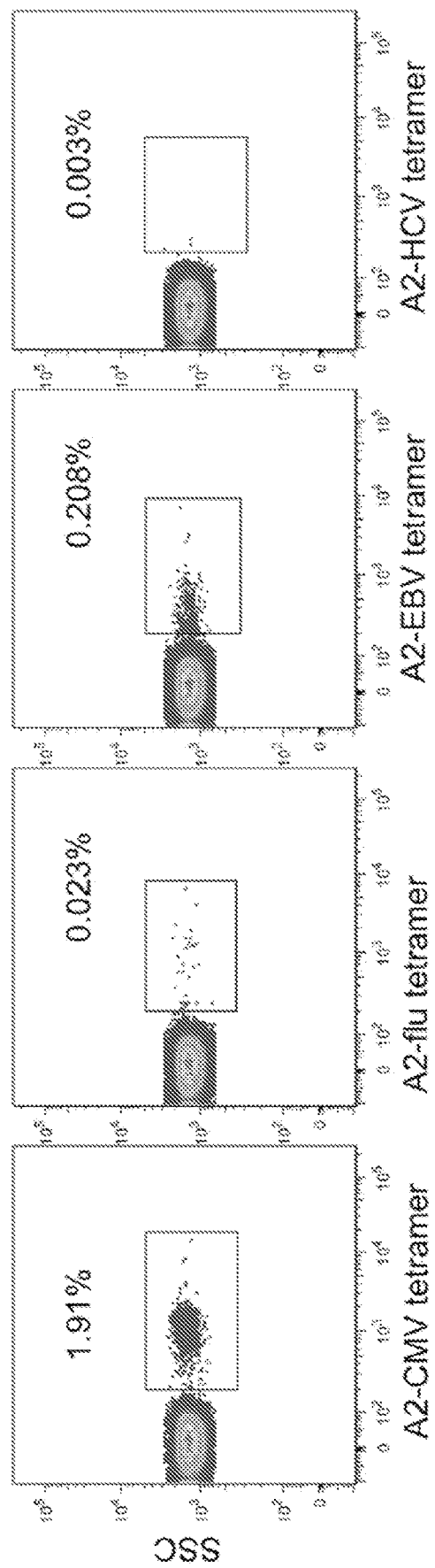
FIG. 2 shows plots of flow cytometry data acquired in experiments testing pMHCI tetramer staining of T cells with various antigen specificities. Peripheral blood mononuclear cells from a cytomegalovirus seropositive (CMV+), A2+ donor were enriched for CD8+ T cells, which were then stained with pMHCI complexes generated by peptide exchange of an MHC allele A2-peptide conjugate with viral peptides.

In further experiments, MHC tetramers were prepared using a streptavidin-dye conjugate (e.g., streptavidin-phycoerythrin) to stain CD8+ T cells isolated from a cytomegalovirus seropositive (CMV+), A2+ healthy donor. Data were collected indicating detection (and therefore presence of) an expanded CMV-specific, but not HCV-specific population of T cells (see, e.g., FIG. 2). This donor also showed flu-specific and Epstein Barr virus (EBV)-specific T-cell populations with moderate sizes (see, e.g., FIG. 2). Taken together, these data indicate that production of peptide-MHC complexes according to the technology described herein was successful.

Example 2—Production of MHCII Proteins

During the development of embodiments of the technology provided herein, experiments were conducted in which CLIP-DR*0101/0401 complexes were purified. The CLIP-DR*0101/0401 complexes were readily peptide-exchangeable to form functional tetramers with TCR-binding specificities (see, e.g., FIG. 3B). Data collected during the experiments indicated that the average yield was approximately 2 mg/L in 5 days, compared to 2-3 months using the current technologies involving use of a CHO cell expression system. Furthermore, some embodiments of the technology comprise use of an enrichment protocol using anti-HIS magnetic beads to provide for the isolation and enrichment of tumor-specific CD4+ T cells from cancer patients and their characterization using metal-tagged antibodies via mass cytometry. Compared to standard anti-fluorophore (PE) enrichment, the anti-HIS beads showed comparable efficiency (see, e.g., FIG. 3B). The data collected indicate that the technology described herein provides a robust system for producing peptide-DR complexes, which are compatible with anti-HIS magnetic bead enrichment. Embodiments further relate to cloning, expressing, and purifying CLIP-DR*0701/1501 complexes.

The pMHC complexes described herein (e.g., pMHCI and pMHCII) find use in antigen-specific (e.g., tumor-specific) T-cell detection and isolation from healthy donors or disease (e.g., cancer) patients. In some embodiments, the pMHC complexes are immobilized on the addressable protein scaffold by fusion of an anchor subunit (e.g., a6) to the pMHC. In some embodiments relating to pMHCII, the anchor subunit (e.g., a6) is fused to the C-terminus of the MHCII DRα chain after the HIS tag (see, e.g., FIG. 3A). In experiments conducted during the development of the technologies described herein, CLIP-DR1-a6 was successfully expressed and purified.

Example 3—Assembly of a pMHC on a Scaffold

During the development of embodiments of the technology described herein, experiments were conducted to assemble a pMHC to the protein scaffold using the anchor subunit-dock subunit technology described herein. In particular, purified CLIP-DR1-anchor subunit (e.g., a6) fusion proteins were loaded on yeast cells displaying a scaffold $(d6)_3$ engineered for protein display. Flow cytometry data indicated a double positive population of cells, which indicated that the CLIP-DR1-anchor subunit (e.g., a6) was anchored to the scaffold protein comprising the appropriate dock subunit (e.g., the binding dock d6 subunit) (see, e.g., FIG. 4).

Example 4—Isolation, Activation, and Characterization of T Cells

During the development of embodiments of the technology provided herein, experiments are conducted to test T cell activation using signals in a bull's-eye pattern presented by the pMHC/CD80/ICAM1 TSPA technology described herein. Experiments use breast cancer as the target malignancy because it is very well studied disease and there is a rich collection of relevant cell lines and animal models available. Using the tetrameric form of the biotinylated pMHC complexes described herein, T cells from peripheral blood of healthy donors are isolated. Tumor-specific T cells are present in healthy donors and have not undergone repeated stimulation, which is desirable for adoptive therapy. Because of the relative naïve phenotype of these tumor-specific T cells, they are found in low frequency and thus a magnetic enrichment step is used before fluorescence-activated cell sorting (FACS). Experiments test five pMHCI complexes: A2 in complex with peptides derived from HER-2/neu, Muc-1, or p53, which are expressed by the breast cancer cell lines MCF-7 and/or MDA-MB-231. The isolated tumor-specific T cells are cultured in complete RPMI media supplemented with 5% autologous serum and 3% IL-2, and repeatedly stimulated with the aAPC once a week for 2-4 weeks. The extent of expansion is compared to that of autologous irradiated PBMC loaded with the aforementioned peptides. Then the expanded T cells are evaluated for killing of MCF-7/MDA-MB-231 cells by chromium-51 cytotoxicity assay, and for phenotype and function using the antibody panel listed in Table 1. The mass cytometry ("CyTOF") antibody panel shown in Table 1 was developed to provide detection of all major CD8+ and CD4+T cell subsets simultaneously and to assess 40 parameters (including 14 phenotypic markers and 17 functional markers) on single cells. The highly multiplexed and high-resolution evaluation of T cell properties provides a technology to pinpoint the phenotypic and functional metrics of T cell subsets that exhibit exquisite anti-tumor reactivity.

TABLE 1

CyTOF antibody panel for T cell phenotypic and function characterization.

| Phenotypic markers | Element tag | Functional markers | Element tag |
|---|---|---|---|
| CD3 | Cd112 | IL-2 | Pr141 |
| CD45RO | Nd144 | TNF-α | Sm152 |
| CD57 | Nd145 | IFN-γ | Nd143 |
| CD8 | Nd146 | IL-4 | Ho165 |
| CD4 | Sm149 | IL-13 | Tm169 |
| CD38 | Eu151 | IL-17A | Yb172 |
| HLA-DR | Sm154 | IL-17F | Tb159 |
| CD62L | Gd156 | IL-17AF | Dy161 |
| CD14/CD33 | Gd157 | IL-10 | Gd155 |
| CD27 | Gd158 | GMCSF | Nd148 |
| CD28 | Gd160 | MIP-1β | Nd150 |
| CCR4 | Dy162 | GranzymeB | Nd142 |
| CD127 | Dy164 | Perforin | Lu175 |
| CD25 | Er166 | CD69 | Sm147 |
| CD45RA | Er167 | CD107a/b | Eu153 |
| CCR7 | Er168 | Other | |
| CXCR3 | Er170 | Viability | In115 |
| CCR6 | Yb171 | DNA | Ir191/193 |
| CD19 | Yb173 | mCD45 | La139 |
| CTLA4 | Yb174 | Retetive cell size | NA |
| CD40L | Yb176 | | |

Identifying metrics of an effective anti-tumor T-cell response is challenging because the responsible anti-tumor T-cell subsets are present at a low frequency. Accordingly, biostatistical approaches are used to isolate them from a large dataset. In some embodiments, analytical strategies previously developed for studying CMV find use to distill useful biological information using PBMCs from healthy donors and the antibody panel listed in Table 1.

Figure 5:
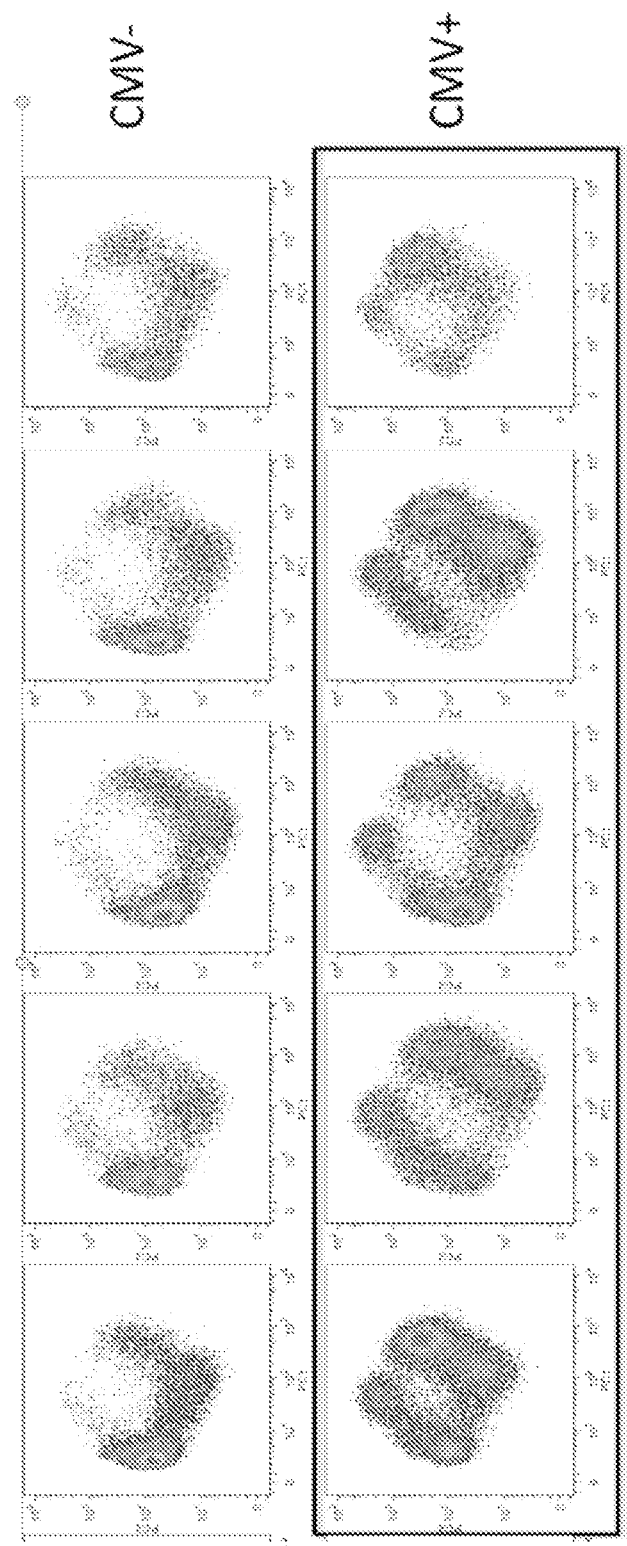
FIG. 5 shows flow cytometry data in which 3D-PCA patterns of CD8+ T cells reveal functional subsets associated with CMV status. Pseudo-colored density-dot plots of total CD8+ T cells showing the five major clusters identified by PCA.

For example, principal component analysis (PCA) revealed that the 31-parameter phenotypic and functional space of the CD8+ T cells forms a continuum and the heterogeneity within the distribution is dynamically arranged into distinct niches of the 3D-PCA space (see, e.g., FIG. 5). This overall structure of the 3D-PCA space is conserved in all healthy donors examined; however, the niches are differentially occupied in CMV+ donors vs. CMV− donors, resulting in apparent patterns associated with CMV status (FIG. 5). Gating on the expanded population revealed three groups of new cytotoxic functional subsets present only in CMV+ donors. A high-resolution linear display of a complete 8-functional repertoire reveals different CD8+ and CD4+ T-cell fingerprints associated with CMV-seropositivity. These CMV-associated patterns and fingerprints have potential use for diagnosis and biomarker screening of CMV infection.

This analytical strategy is applicable to the present technology to identify immune functional subsets associated with an effective anti-tumor response, which finds use as a screening criterion for high-throughput cancer immunotherapy engineering.

Furthermore, the expanded T cells showing cytotoxicity towards in vitro cultured cancer cell lines are further evaluated for tumor regression using human breast-cancer xenograft mice. In particular, MCF-7/MDA-MB-231 cells mixed with tumor-specific or non-specific CD8+ T cells are implanted in the mammary fat pad of NOD/SCID mice. The mice are evaluated daily for development and size of the tumors, and the results are compared between the two groups. T cells are also evaluated for anti-tumor activity using an experimental pulmonary metastasis model. The NOD/SCID mice are given an intravenous injection of cancer cells to establish pulmonary metastasis. Five days after injection, the T cells are adoptively transferred, and the mice are evaluated for tumor development and survival. The mice are examined daily and morbid mice are euthanized, and their lungs weights are recorded. Surviving mice are euthanized on days 6, 12 and 16, and their lungs are examined for tumor-induced histopathological changes. These experiments provide an evaluation of the anti-tumor activity of the TSPA-expanded T cells in vivo, and thus provide for the identification and testing of anti-tumor T-cell metrics.

In vitro expansion of T cells with TSPA presenting IS patterns provides an improved activation and expansion of T cells, e.g., relative to expansion with polystyrene beads uniformly coated with T-cell activating proteins. our TSPAs should achieve better T-cell activation/expansion.

In some embodiments, both CD8+ and CD4+ T cells are activated and transferred into a subject. For example, CD4+ T cells positively influence infiltration and persistence of the CD8+ T cells in a tumor mass possibly by secreting cytokines such as IL-2, which promotes proliferation of the CD8+ T cells. Therefore, embodiments comprise generating tumor-antigen specific CD4+ T cells using TSPAs and co-adoptive transfer of both tumor-specific CD8+ and CD4+ T cells (e.g., in mice with pulmonary metastases). In some embodiments, overlapping 20-mer peptides are rapidly exchanged into the CLIP-MHCII protein constructs for epitope screening.

Example 5—TSPA Configuration and Anti-Tumor T-Cell Response

During the development of embodiments of the technology, the analytical procedure developed in the experiments described above is used to produce a pMHC-CD137L-ICAM1 TSPA with a bull's-eye pattern and a pMHC-CD80-ICAM1 TSPA with a homogeneous pattern. Experiments are conducted to compare the T-cell conditioning capabilities of these two systems to that of the pMHC-CD80-ICAM1 bull's-eye TSPA. CD137L has been shown to activate and expand distinct populations of T cells from CD80; accordingly, the differing compositions and patterns produce significant differential functional outcomes of the anti-tumor activity of T cells expanded using the three TSPAs with different composition and presentation patterns. The resulting high-dimensional phenotype/function profiles of T cells with different levels of killing activity are compared to define the relationship between TSPA configuration and the anti-tumor activity of expanded T cells using various biostatistics tools, including PCA, t-tests, and elastic-net logistic regression models. For example, different types of T-cell subsets are identified using established cell markers as shown in Table 1. Then, for each T-cell subset, data are pooled from 15-20 donors and PCA analysis is performed as described herein to identify subpopulations responsible for potent anti-tumor activity. Statistical significance of the clustering is assessed using resampling tests based on parametric bootstrapping with parameters estimated by assuming there is only a single cluster. Finally, the data for each patient are summarized as a vector of proportion of cells in each subpopulation of all T-cell subsets, and t-tests and elastic-net logistic regression models are applied to select the subset of subpopulations that predict effective anti-tumor response. The selected predictors provide information (e.g., by using logistic regression) that find use in predicting the therapeutic effectiveness of TSPAs with different ligand composition and presentation patterns, e.g., for each donor. The prediction accuracy, as well as sensitivity and specificity, are evaluated using receiver operating characteristic (ROC) analysis.

Example 6—Use of TSPA for T-Cell-Based Personalized Immunotherapy Engineering The continuously expanding list of T-cell co-stimulation proteins presented in many different immunological synapse patterns collectively protect people from a wide spectrum of pathogens. This indicates that particular combinations of costimulation proteins provided in particular presentation patterns offer protection against specific antigens. Using the T-cell subpopulations identified in experiments conducted as described above as a screening surrogate of effective anti-tumor response, the modular nature and the yeast-surface displayed format of the TSPA are used to create and screen a large number of co-stimulation proteins presented in different patterns. This approach represents a powerful high-throughput tool for personalized cancer immunotherapy engineering.

During the development of embodiments of the technology described herein, addressable protein scaffolds are tested comprising, e.g., a multifocal or a polarized pattern. The scaffolds are assembled using the same anchor (e.g., a1-a6) and dock (e.g., d1-d6) orthogonal pairs described herein fused in an order to provide the appropriate pattern. First, the primary anchor protein is displayed on the yeast cell surface, then the purified dock proteins loaded and assembled. Flow cytometry and STED microscopy are used to monitor and verify the assembly steps.

In addition to pMHC, an array of stimuli has been shown to produce a productive T cell activation. For example, the costimulatory protein CD80 and the adhesion protein ICAM1 are among the best characterized. Accordingly, embodiments of the technology provide co-presentation of CD80 and ICAM1 with pMHC. Additional embodiments comprise use of the T-cell-activating ligands CD40, CD86, ICOSL, GITRL, OX40L, etc. In some embodiments, the extracellular domains of these proteins are fused to a particular anchor subunit and a HIS tag, expressed in insect cells, and purified using nickel-affinity and size-exclusion chromatography. The function of the resulting recombinant fusion proteins is tested by staining human T cells isolated from human blood using fluorescent anti-HIS antibody as a secondary antibody. The signals are compared to their respective antibody staining of the human T cells.

Moreover, during the development of embodiments of the technology provided herein, combinations of co-stimulation proteins self-assembled into different presentation patterns are tested. For example, data are gathered from experiments testing homogeneous, bull's eye, multifocal, or polarized arrangements of the pMHC and co-stimulation proteins. Assembly of the TSPA is evaluated by flow cytometry analysis of each of the individual protein ligands and STED microscopy for the overall structure. Data are collected on the functional outcomes of tumor-specific T cells expanded using the different configurations of TSPAs with different ligand composition and presentation patterns. The experimental and analytical approaches described above find use in collecting data on T-cell cytotoxicity towards in vitro cultured breast cancer cell lines MCF-7 and MDA-MB-231, tumor regression in human xenograft mouse models, tumor regression in experimental metastasis mouse models, and the phenotype and function of CD8+ and CD4+ subpopulations (e.g., as defined above). Further, PCA, t-tests, elastic-net logistic regression models, and ROC analysis find use to distill relevant parameters and establish their correlation with grouped TSPA compositions and patterns. Through these correlations, the ligand compositions and presentation patterns associated with effective antitumor T-cell activity are identified.

Example 7—Class II pMHC Protein

Figure 6:
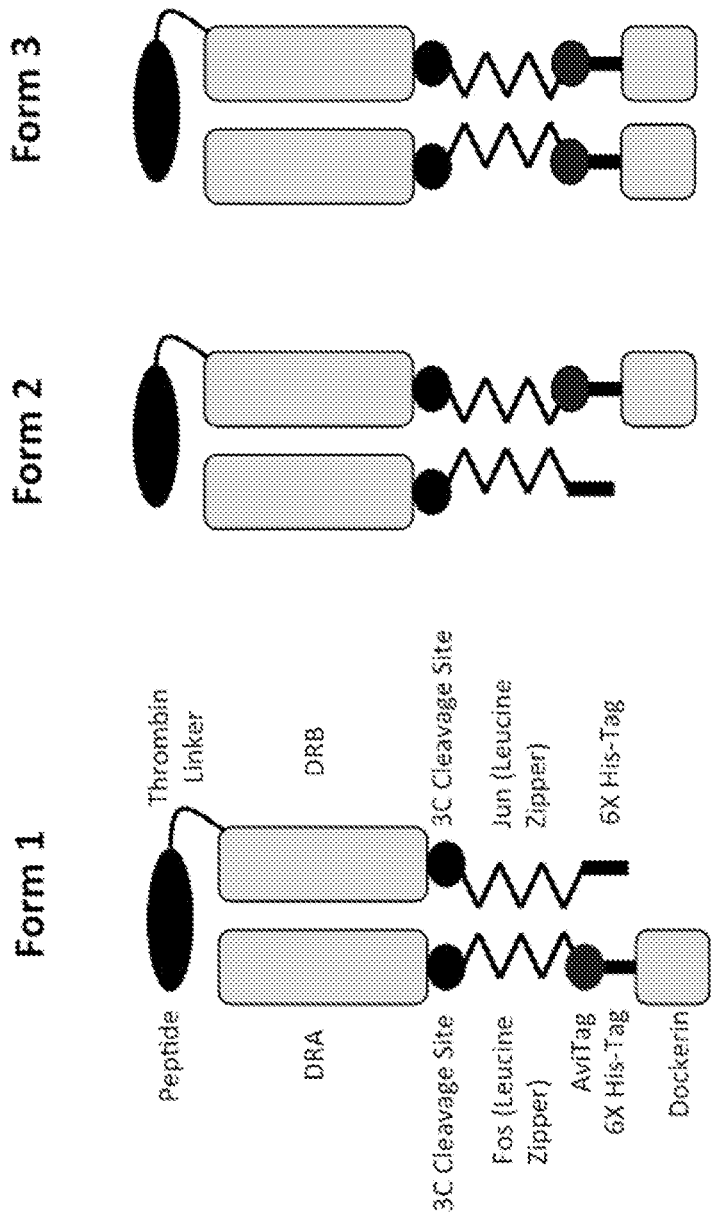
FIG. 6 show schematic drawings of three forms of a class II pMHC protein described herein.

Some embodiments relate to the design and synthesis of a class II pMHC protein. Various embodiments comprise the dock subunit (FIG. 6, "Dockerin") on the alpha subunit (FIG. 6, "Form 1"), on the beta subunit (FIG. 6, "Form 2"), and on both the alpha and the beta subunits (FIG. 6, "Form 3"). Sequences and sources of some components are described in Example 8.

Example 8—Peptide Sequences

Table 2 provides the sources of sequences that find use in embodiments of the constructs provided herein. Further, some embodiments comprise polypeptides comprising sequences obtained from the Immune Epitope Database and Analysis Resource (IEDB) available on the internet. Additionally, the following peptide sequences are incorporated herein by reference from the IEDB: HA, epitope number 48237; CLIP, epitope number 119507; MBP, epitope number 13572; NP, epitope number 97487.

TABLE 2

| Component | UniProtKB | Protein Residue | Comments | URL Link |
|---|---|---|---|---|
| CLIP | P04233 | 103-117 | Invariant Chain | uniprot.org/uniprot/P04233 |
| Thrombin Linker | | | LVPRGS (SEQ ID NO: 6) | |
| DRB1*01 | A9JJF6 | 30-227 | Ectodomain | uniprot.org/uniprot/A9JJF6 |
| DRB1*04 | | | Ectodomain | uniprot.org/uniprot/ |
| DRB1*07 | | | Ectodomain | uniprot.org/uniprot/ |
| DRB1*15 | | | Ectodomain | uniprot.org/uniprot/ |
| 3C cleavage site | * | * | LEVLFQGP (SEQ ID NO: 7) | |
| Jun (leucine zipper) | P05627 | 279-318 | | uniprot.org/uniprot/P05627 |
| Fos (leucine zipper) | P01101 | 161-200 | | uniprot.org/uniprot/P01101 |
| DRA | P01903 | 26-216 | Ectodomain | uniprot.org/uniprot/P01903 |
| AviTag | * | * | GLNDIFEAQKIEWHE (SEQ ID NO: 8) | avidity.com/ |
| Dockerin | P0C2S5 | 673-751 | Dockerin subunit | uniprot.org/uniprot/P0C2S5 |

Example 9—Assembly of Cell Surface Scaffold

Figure 7:
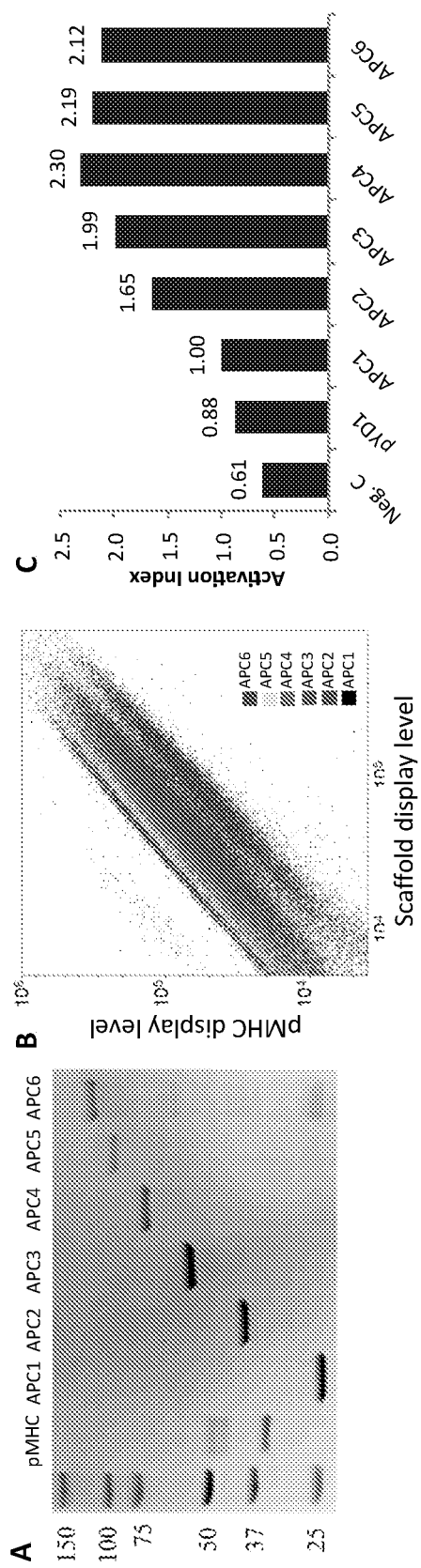
FIG. 7 shows data indicating the assembly of a soluble scaffold comprising pMHC and 1 to 6 dock proteins (e.g., FIG. 7A), a scaffold comprising pMHC and 1 to 6 dock proteins assembled on the surface of a yeast cell (e.g., FIG. 7B), and T cell activation (e.g., FIG. 7C) by scaffolds comprising from one to six dock proteins on a primary anchor protein.

During the development of embodiments of the technology provided herein, experiments were conducted to test the assembly of a soluble scaffold comprising pMHC and 1 to 6 dock proteins (e.g., FIG. 7A), a scaffold comprising pMHC and 1 to 6 dock proteins assembled on the surface of a yeast cell (e.g., FIG. 7B), and T cell activation (e.g., FIG. 7C) by scaffolds comprising from one to six dock proteins on a primary anchor protein. The data indicate that technology provides for tuning the number (n) of pMHC protein in the presentation complex. FIG. 7C shows data indicating that by increasing the n value from 1 to 6, the antigen-specific T-cell response increases and plateaus when n=4.

Example 10—Production of Components of the aAPC System

The technology provides an artificial antigen-presenting system (aAPC) comprising components assembled according to orthogonal, high-affinity ($K_d \sim 10^{-9}$ to $10^{-12}$ M or stronger) interactions between the dock subunits and anchor subunits. Embodiments provide dock subunits and anchor subunits that direct the assembly of T-cell activating proteins into a supramolecular IS-mimicking pattern.

Figure 8:
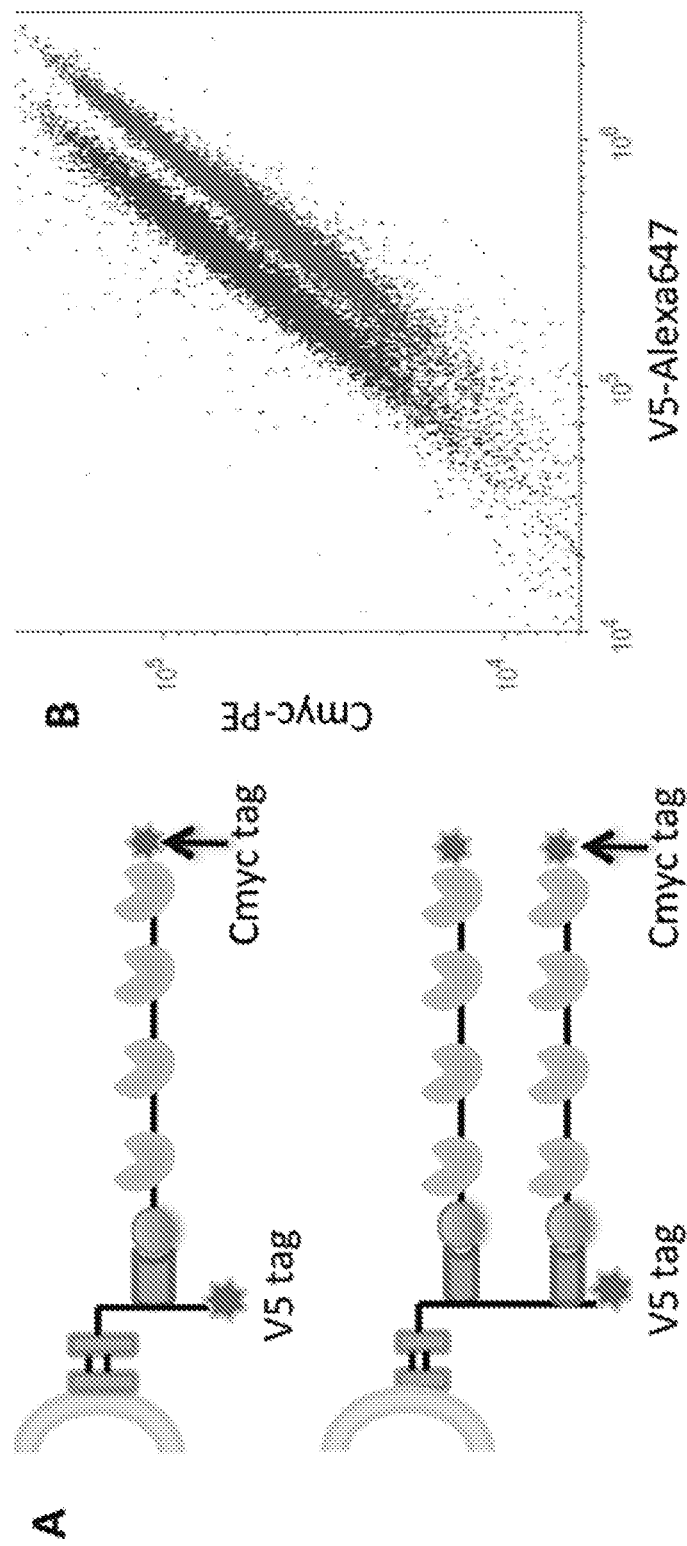
FIG. 8 shows display of a protein scaffold on a yeast cell surface.

During the development of embodiments of the technology, experiments were conducted to design, express, and assemble primary scaffold (primary anchor) proteins with varying binding capacity, e.g., $(aA1)_1$ and $(aA1)_2$. These scaffold proteins bind one or two copies of the soluble secondary scaffold (dock) protein $dA1\text{-}(dA2)_4$, respectively, by interactions between the dA1 dock subunit and the aA1 anchor subunits (FIG. 8). In particular, V5 and C-myc tags fused to the C-terminus of the primary scaffold proteins (primary anchor protein) and secondary scaffold proteins (dock proteins), respectively, provided for the detection and visualization of the 2D scaffold assembly (FIG. 8A). FIG. 8A is a schematic representation of the scaffold comprising an $(aA1)_1$ (top) or $(aA1)_2$ (bottom) protein tagged with a V5 epitope and a soluble $dA1\text{-}(dA2)_4$ protein tagged with a Cmyc epitope.

Data collected during the experiments indicated that both $(aA1)_1$ and $(aA1)_2$ primary scaffold proteins were displayed on the yeast cell surface and bound the expected number of the soluble secondary scaffold protein $dA1\text{-}(dA2)_4$ (FIG. 8B). FIG. 8B is flow cytometry data collected from yeast cells displaying the scaffold and that were co-stained with anti-V5 and anti-Cmyc antibodies. The parallel staining pattern of the $(aA1)_2\text{-}dA1\text{-}(dA2)_4$ (upper left cloud of data points) and $(aA1)\text{-}dA1\text{-}(dA2)_4$ (lower right cloud of data points) indicates the successful assembly of the 2D scaffold with the design shown in FIG. 8A. Accordingly, the data demonstrate assembly of the scaffold assembly as described herein.

To assemble additional scaffolds, the technology provides for display of the anchor and dock building blocks on the yeast cell surface or purified in a soluble form. Accordingly, experiments conducted during the development of the technology provided cloned constructs and verified the display and assembly of four other anchor-dock pairs (e.g., aA2-dA2, aB1-dB1, aC1-dC1, and aD1-dD1). These components provide the building blocks of longer primary scaffold proteins to be displayed on the yeast cell surface.

Example 11—Class I and Class II Peptide-MHC Complexes

Embodiments of the technology relate to an aAPC system comprising functional peptide-MHC (pMHC) complexes on a cell surface to engage a T-cell receptor. MHC molecules are both polygenic and highly polymorphic, and are capable of binding an array of different peptides. Therefore, the technology provides an easy to use and high-throughput system for generating a large panel of pMHC complexes.

Figure 9:
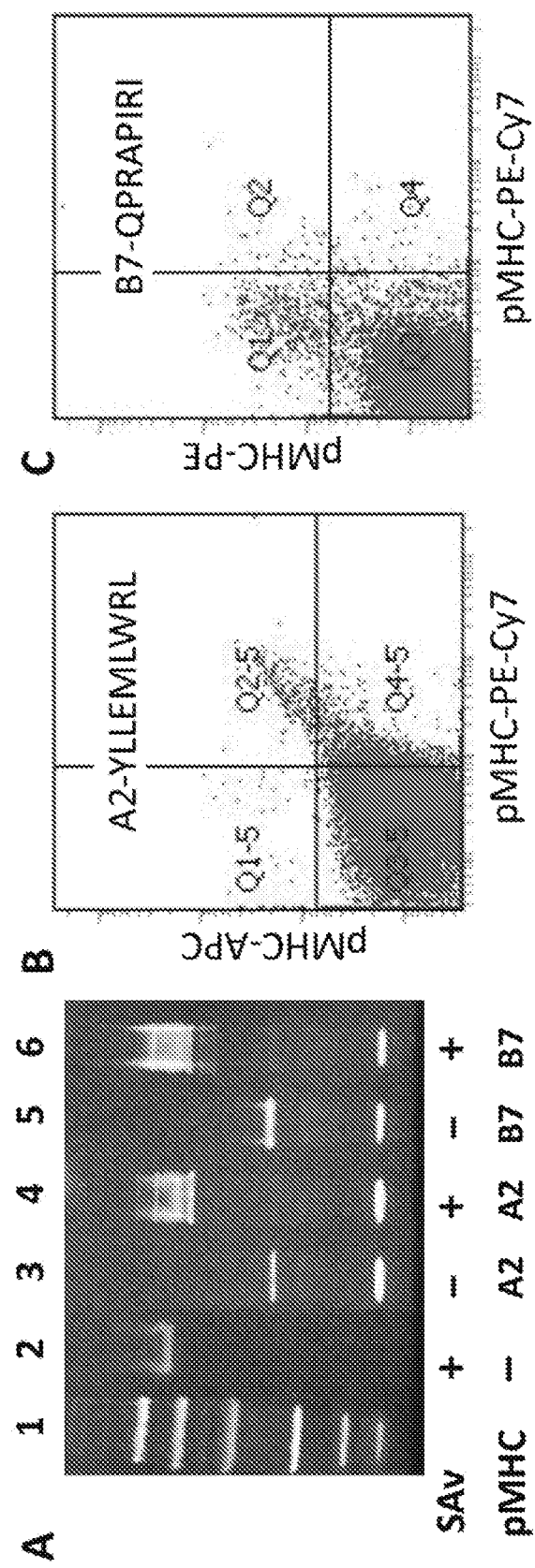
FIG. 9 shows the production of functional A2 and B7 MHCI proteins in complex with an exchangeable peptide upon UV irradiation.

In particular, during the development of embodiments of the technology described herein, experiments were conducted to design and test an E. coli based expression system to make A*0201 (~30% allele frequency in Caucasians) and B*0702 (13% allele frequency in Caucasians) with a UV-cleavable peptide. The data collected indicated that both constructs, A2-GILGFVFJL (SEQ ID NO: 4) and B7-AARGJTLAM (SEQ ID NO: 5) are successfully biotinylated (FIG. 9A), readily exchangeable with peptides of interest, and bind specific T cells (FIG. 9B and FIG. 9C). In particular, the data indicated the production of functional A2 and B7 MHCI proteins in complex with an exchangeable peptide upon UV irradiation (FIG. 9). Biotinylation of the MHCI proteins was successful (FIG. 9A) and the biotinylated A2 (FIG. 9B) and B7 (FIG. 9C) proteins were exchanged with a binding EBV epitope. Experiments testing for staining of PBMCs from healthy donors indicated the specific binding of antigen-specific T cells (FIG. 9B; FIG. 9C).

Figure 10:
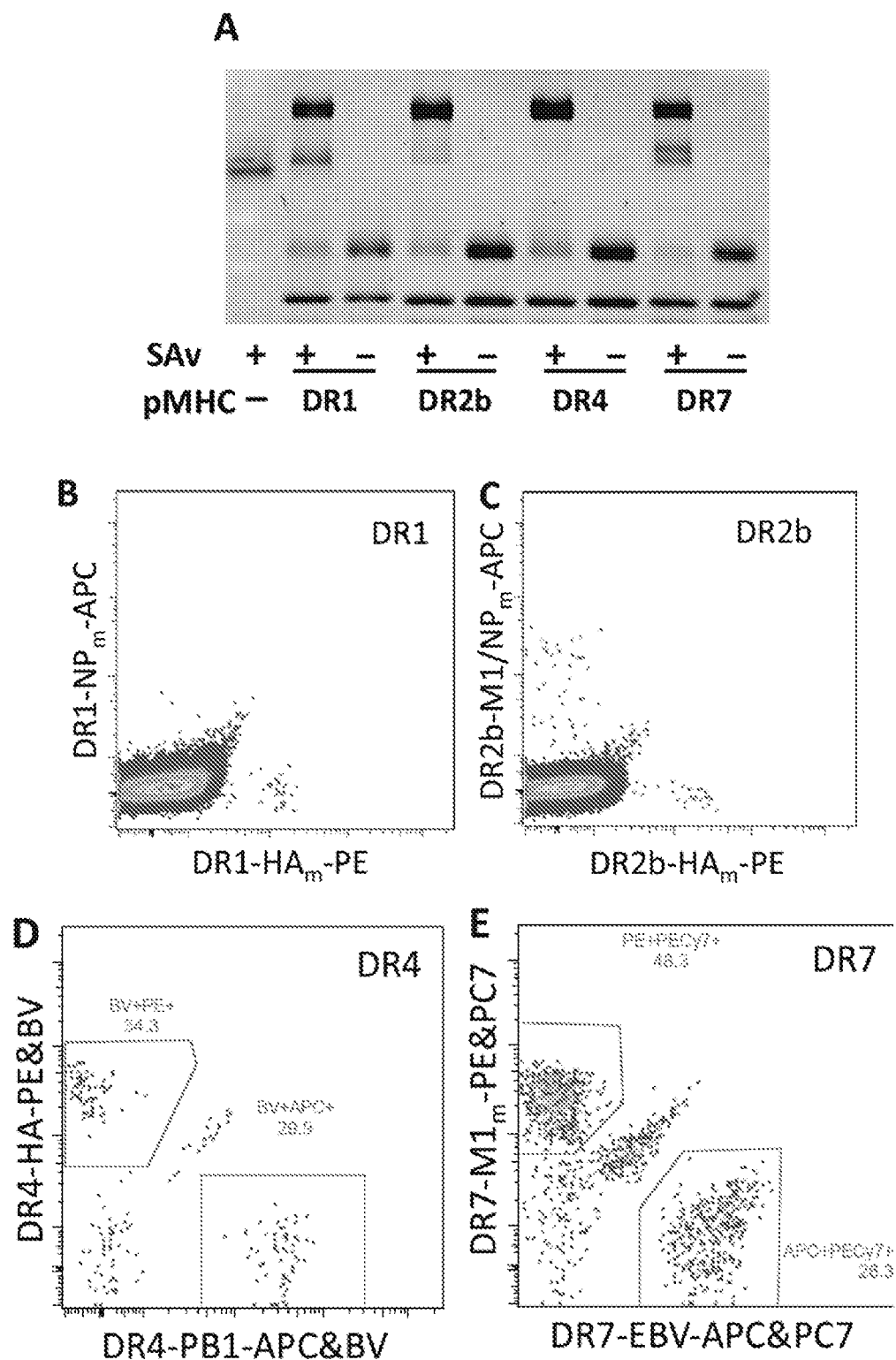
FIG. 10 shows the production of functional DR1, DR2b, DR4, and DR7 MHCII proteins in complex with an exchangeable peptide CLIP upon enzymatic cleavage.

For class II pMHC, experiments were conducted to design and test an expression system based on an enzymatically cleavable CLIP-MHCII construct in insect cells to produce four different alleles, including DR*0101 (~9% allele frequency in Caucasians), DR*0401 (~5% allele frequency in Caucasians), DR*0701 (~11% allele frequency in Caucasians), and DR*1501 (~14% allele frequency in Caucasians). The conventional names DR1, DR4, DR7, and DR2b are used herein for these four alleles, respectively. This construct provides for exchange of the CLIP peptide with any T-cell epitope of interest upon enzymatic cleavage of the CLIP peptide to create a panel of pMHCII complexes. Data demonstrated that all four DR alleles are successfully biotinylated (FIG. 10A), readily exchangeable with peptides of interest, and bind antigen specific T cells (FIG. 10B to FIG. 10E). In particular, the data indicated the production of functional DR1, DR2b, DR4, and DR7 MHCII proteins in complex with an exchangeable peptide CLIP upon enzymatic cleavage. MHCII proteins were biotinylated to an extent of greater than 90% (FIG. 10A). The biotinylated CLIP-DR proteins were exchanged with a binding epitope from different viruses, including influenza (HA, NP, M1, and PB1) and EBV, and then tested for staining of PBMCs from healthy donors (FIGS. 10B to 10E). Due to the low frequency of CD4+ T cells, several peptides were pooled for a particular allele as indicated by the subscript "m" of a viral protein. In addition, for DR4 and DR7, the same pMHC complexes were labeled with two different fluorophores. For example, DR4-PB1-specific T cells showed a double staining of APC and BV (brilliant violet) in FIG. 10D.

Figure 11:
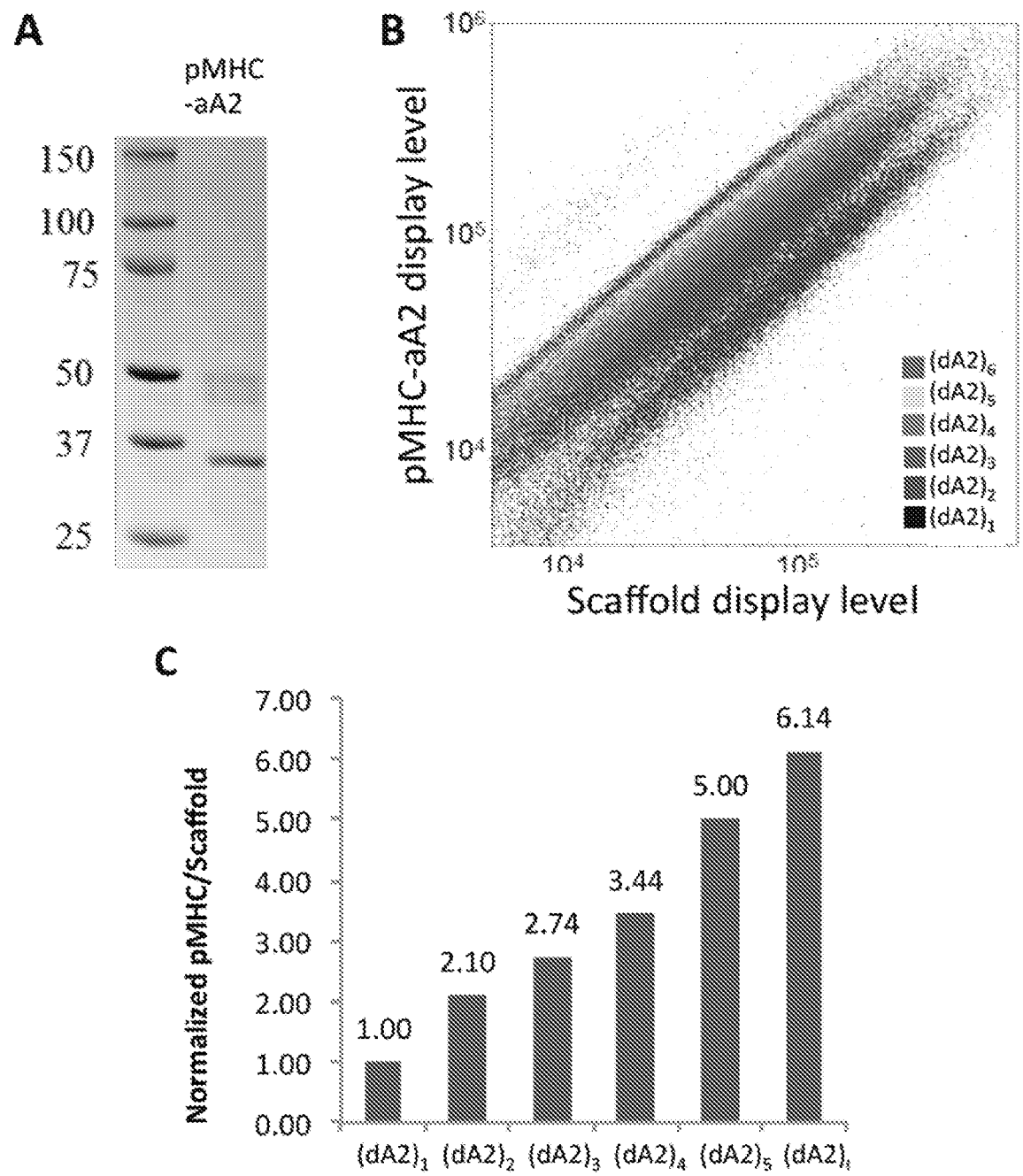
FIG. 11 shows assembly of $(dA2)_n$-$(pMHC)_n$ supramolecular complexes directed by the interactions between the dock subunits and anchor subunits.
Figure 12:
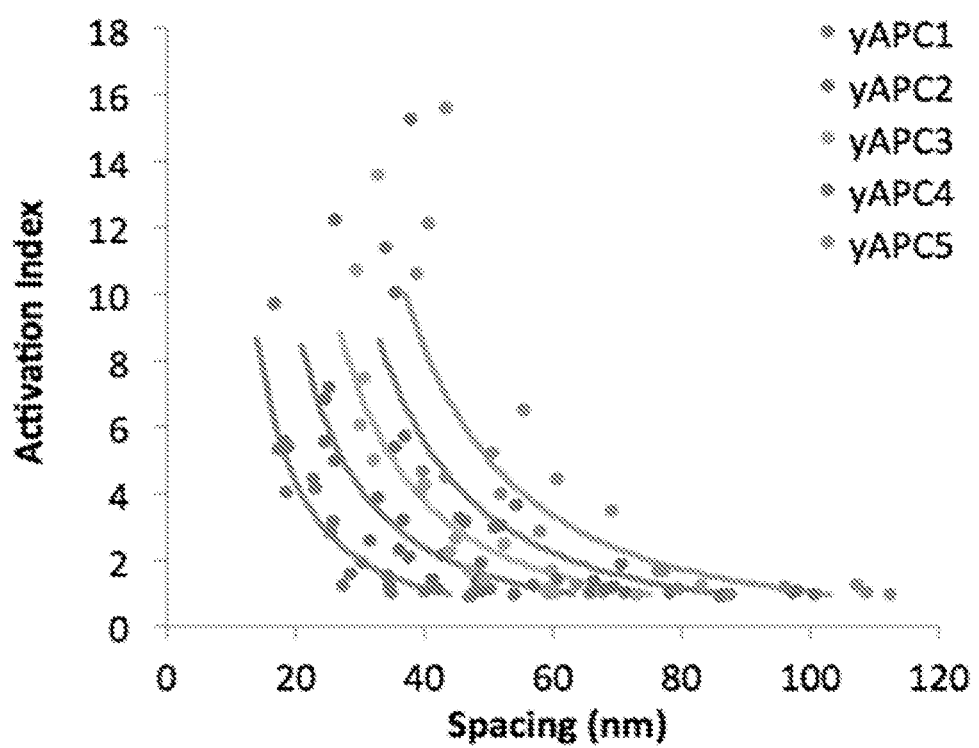
FIG. 12 is a plot showing the tunable response ("Activation Index") of antigen specific T cells to the engineered artificial antigen presenting cells. In particular, transgenic T cells expressing T cell receptor specific to DR1-HA showed a tunable response ("Activation Index") to engineered yeast artificial antigen presenting cells displaying varying pMHC in configurations ("Spacing") as described in FIG. 11. Data and lines fitting the data are shown from left to right for yAPC1, yAPC2, yAPC3, yAPC4, and yAPC5, respectively.

The pMHC complexes find use for tumor-specific T-cell detection and isolation from healthy donors or cancer patients. Furthermore, embodiments provide that an anchor subunit aA2 is fused to the pMHC complex. Experiments conducted during the development of embodiments of the technology indicated that the pMHC-aA2 fusion protein was successfully purified from an insect cell expression system and showed binding to the protein scaffold to form complexes with varying degrees of complexity (FIG. 11). Assembly of $(dA2)_n$-$(pMHC)_n$ supramolecular complexes was successfully directed by the interactions between the dock subunits and anchor subunits. FIG. 11A shows an SDS-PAGE gel of the pMHC-aA2 fusion protein showing two subunits with expected sizes; FIG. 11B shows data from yeast cells displaying the $(dA2)_n$-$(pMHC)_n$ supramolecular complexes and costained with anti-V5 (for scaffold $(dA2)_n$ display level) and anti-His (for pMHC display level) antibodies. The parallel staining pattern indicated the successful assembly of the $(dA2)_n$-$(pMHC)_n$ supramolecular complexes, which is further confirmed using fluorescence quantification beads as shown in FIG. 11C.

Example 12—Assembly of the Supramolecular Bull's-Eye Pattern

During the development of embodiments of the technology, experiments tested assemblies of primary scaffold proteins (e.g., $(aA1)_1$ and $(aA1)_2$) secondary scaffold proteins (e.g., $dA1$-$(dA2)_4$), and pMHC complexes fused with an anchor subunit (e.g., aA2). In particular, data were collected indicating that the orthogonal, high-affinity interactions between the dock subunits and anchor subunits direct the self-assembly of T cell activating proteins into a defined pattern. In the experiments, scaffold proteins were constructed and displayed on yeast cell surface: $(dA2)_1$, $(dA2)_2$, $(dA2)_3$, $(dA2)_4$, $(dA2)_5$ and $(dA2)_6$. $(dA2)_4$ is shown in FIG. 8A schematically and the other scaffold proteins differ by the number of dock subunits as indicated by the subscript number. Under saturation loading conditions, the display capacity of the scaffold protein increases with the number of dock subunits (FIG. 11). Using fluorescence quantification beads, the scaffold protein $(dA2)_n$ showed binding of n copies of the pMHC complexes (FIG. 11C). These results indicate successful supramolecular pattern assembly directed by the interactions between the dock and anchor subunits.

In additional experiments, the soluble version of these scaffold proteins are prepared and are examined by gel mobility shift assay and stimulated emission depletion (STED) microscopy. In parallel, the ability of yeast cells displaying the $(dA2)_n$-$(pMHC)_n$ supramolecular complexes is tested for activating antigen-specific T cells by measuring the expression of activation markers, including CD69, IFNγ, and/or IL2. It is contemplated that T-cell activation will increase with an increasing value of n due to improved engagement of T cell receptor.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A composition for activating a T cell with an antigenic peptide specific for said T cell, the composition comprising:
   a) a cell-expressed primary anchor protein comprising a first anchor subunit;
   b) a dock protein comprising:
      1) a first dock subunit that is an orthogonal binding partner of the first anchor subunit; and
      2) a second dock subunit; and
   c) a pMHC complex made by a process of binding an antigenic peptide to a MHC polypeptide and selecting the pMHC complex that activates a T cell, wherein the pMHC complex further comprises a second anchor subunit that is an orthogonal binding partner of the second dock subunit, wherein the first dock subunit and the first anchor subunit are selected from the group of orthogonal binding pairs consisting of: cohesion and dockerin; SH3 ligand and SH3 domain; PDZ ligand and PDZ domain; and antigen and antibody or antigen-binding antibody fragment specific for the antigen; and wherein the second dock subunit and the second anchor subunit are selected from the group of orthogonal binding pairs consisting of cohesion and dockerin; SH3 ligand and SH3 domain; PDZ ligand and PDZ domain; and antigen and antibody or antigen-binding antibody fragment specific for the antigen.

2. The composition of claim 1 wherein the primary anchor protein is a fusion protein comprising a protein sequence for cell surface display of the primary anchor protein.

3. The composition of claim 1 wherein the primary anchor protein is a fusion protein comprising a portion encoding a yeast mating protein.

4. The composition of claim 1 wherein the primary anchor protein is a fusion protein comprising a portion encoding yeast Aga2p.

5. The composition of claim 1 wherein the primary anchor protein comprises an epitope tag and/or the dock protein comprises an epitope tag.

6. The composition of claim 5 wherein the epitope tag is V5 or c-myc.

7. The composition of claim 1 wherein the dock protein comprises a histidine tag and/or the pMHC complex comprises a histidine tag.

8. A composition for activating a T cell with an antigenic peptide specific for said T cell, the composition comprising:
   a) a cell-expressed primary anchor protein comprising a first anchor subunit, a second anchor subunit, and a third anchor subunit;
   b) a first dock protein comprising:
      1) a first dock subunit that is an orthogonal binding partner of the first anchor subunit; and
      2) a fourth dock subunit;
   c) a second dock protein comprising:
      1) a second dock subunit that is an orthogonal binding partner of the second anchor subunit; and
      2) a fifth dock subunit;
   d) a third dock protein comprising:
      1) a third dock subunit that is an orthogonal binding partner of the third anchor subunit; and
      2) a sixth dock subunit;
   e) a first co-stimulatory molecule comprising a fourth anchor subunit that is an orthogonal binding partner of the fourth dock subunit;
   f) a second co-stimulatory molecule; or a co-inhibitory molecule that is B7-H1 (PD-L1) or Galectin-9, said second co-stimulatory molecule or said co-inhibitory molecule comprising a fifth anchor subunit that is an orthogonal binding partner of the fifth dock subunit; and
   g) a pMHC complex made by a process of binding an antigenic peptide to a MCH polypeptide and selecting the pMHC complex that activates a T cell, wherein said pMHC complex further comprises a sixth anchor subunit that is an orthogonal binding partner of the sixth dock subunit,
   wherein the first dock subunit and the first anchor subunit, the second dock subunit and the second anchor subunit, the third dock subunit and the third anchor subunit, the fourth dock subunit and the fourth anchor subunit, the fifth dock subunit and the fifth anchor subunit, and the sixth dock subunit and the sixth anchor subunit are each independently selected from the group of orthogonal binding pairs consisting of: cohesion and dockerin; SH3 ligand and SH3 domain; PDZ ligand and PDZ domain; and antigen and antibody or antigen-binding antibody fragment that is specific for the antigen.

9. The composition of claim 8 wherein the first co-stimulatory molecule is CD30L, CD70, TL1A, CD137L, ICAM1, CD80, CD40, CD86, ICOSL, GITRL, or OX40L.

10. The composition of claim 8 wherein the second co-stimulatory molecule is CD30L, CD70, TL1A, CD137L, ICAM1, CD80, CD40, CD86, ICOSL, GITRL, or OX40L.

11. The composition of claim 8 wherein the first co-stimulatory molecule and the pMHC complex are arranged in a bulls-eye pattern.

12. The composition of claim 8 wherein the first dock protein, the second dock protein, the third dock protein, the first co-stimulatory molecule, and the pMHC complex are expressed as soluble proteins.

13. The composition of claim 1, further comprising a co-stimulatory molecule.

14. The composition of claim 1, wherein the MHC is encoded by HLA-A*0201, HLA-B*0702, HLA-DR*0101, HLA-DR*0401, HLA-DR*0701, or HLA-DR*1501.

15. The composition of claim 8, wherein the MHC is encoded by HLA-A*0201, HLA-B*0702, HLA-DR*0101, HLA-DR*0401, HLA-DR*0701, or HLA-DR*1501.

\* \* \* \* \*